United States Patent
Beeson et al.

(10) Patent No.: US 11,771,916 B2
(45) Date of Patent: Oct. 3, 2023

(54) INTERSTITIAL PHOTODYNAMIC THERAPY

(71) Applicant: Simphotek, Inc., Newark, NJ (US)

(72) Inventors: Karl Beeson, Princeton, NJ (US); Evgueni Parilov, Brooklyn, NY (US); Mary Potasek, Princeton, NJ (US)

(73) Assignee: SIMPHOTEK, INC., Newark, NJ (US)

( * ) Notice: Subject to any disclaimer, the term of this patent is extended or adjusted under 35 U.S.C. 154(b) by 0 days.

(21) Appl. No.: 18/041,079

(22) PCT Filed: Aug. 10, 2021

(86) PCT No.: PCT/US2021/045341
§ 371 (c)(1),
(2) Date: Feb. 9, 2023

(87) PCT Pub. No.: WO2022/039973
PCT Pub. Date: Feb. 24, 2022

(65) Prior Publication Data
US 2023/0238099 A1    Jul. 27, 2023

Related U.S. Application Data

(60) Provisional application No. 63/066,895, filed on Aug. 18, 2020.

(51) Int. Cl.
  *A61N 5/06* (2006.01)
  *G16H 20/10* (2018.01)
  *A61N 5/067* (2006.01)

(52) U.S. Cl.
  CPC .......... *G16H 20/10* (2018.01); *A61N 5/0601* (2013.01); *A61N 5/062* (2013.01); *A61N 5/067* (2021.08);
(Continued)

(58) Field of Classification Search
  CPC ........ A61N 5/06; A61N 5/0601; A61N 5/062; A61N 2005/0626; A61N 2005/0627;
(Continued)

(56) References Cited

U.S. PATENT DOCUMENTS 8,986,358 B2 * 3/2015 Svanberg ............... A61N 5/062
607/92
2010/0329524 A1 * 12/2010 Swartling ............ A61N 5/0601
382/128
(Continued)

FOREIGN PATENT DOCUMENTS

WO        2020097186 A1    5/2020

OTHER PUBLICATIONS

International Search Report and Written Opinion issued in corresponding International Patent Application No. PCT/US21/45341 dated Nov. 26, 2021, 13 pages.
(Continued)

*Primary Examiner* — Ahmed M Farah
(74) *Attorney, Agent, or Firm* — Morgan, Lewis & Bockius LLP

(57) ABSTRACT

A method of administering interstitial photodynamic therapy to a target region of a patient may include receiving information associated with the target region, an initial photosensitizer concentration, a plurality of initial photosensitizer photokinetic rate parameters, and a threshold treatment dose for a photosensitizer, the threshold treatment dose being a threshold photodynamic therapy-dose or a threshold reactive oxygen species dose. A location in the target region for inserting at least one interstitial treatment fiber to deliver the treatment light, and initial values for treatment light transmission is determined. Computational spatial elements are determined for the target region and for the location of emitting surfaces of the at least one interstitial treatment
(Continued)

fiber, and a light fluence rate for delivering treatment light to each of the computational spatial elements. A treatment dose is determined based on the light fluence rate, the plurality of photosensitizer photokinetic rate parameters, and a photokinetic rate equation.

12 Claims, 17 Drawing Sheets

(52) U.S. Cl.
CPC ............... *A61N 2005/063* (2013.01); *A61N 2005/0626* (2013.01); *A61N 2005/0651* (2013.01)

(58) Field of Classification Search
CPC .... A61N 2005/06228; A61N 2005/063; A61N 5/067; A61K 41/0057; A61K 41/0085; G16H 20/10
USPC ..................................................... 607/88–92
See application file for complete search history.

(56) References Cited

U.S. PATENT DOCUMENTS

| | | |
|---|---|---|
| 2011/0034971 A1 | 2/2011 | Svanberg et al. |
| 2018/0207442 A1* | 7/2018 | Shafirstein ........... A61N 5/0601 |
| 2020/0046997 A1* | 2/2020 | Shafirstein ............. A61N 5/062 |

OTHER PUBLICATIONS

Beeson et al., Validation of combined Monte Carlo and photokinetic simulations for the outcome correlation analysis of benzoporphyrin derivative-mediated photodynamic therapy on mice. Journal of biomedical optics 24.3 (2019): 035006, p. 2-7 [online] <DOI: 10.1117/1.JBO.24.3.035006>, 10 pages.

Kim et al., "Light sources and dosimetry techniques for photodynamic therapy." Photochemistry and photobiology 96.2 (2020): 280-294, entire document. [online] <DOI: 10.1111/php.13219>, 15 pages.

* cited by examiner

INTERSTITIAL PHOTODYNAMIC THERAPY

CROSS REFERENCE TO RELATED APPLICATIONS

This application is a 371 of International Patent Application No. PCT/US2021/045341 filed on Aug. 10, 2021, which claims the benefit of priority to U.S. Provisional Application No. 63/066,895, filed on Aug. 18, 2020, the entirety of each is incorporated herein by reference for all purposes.

STATEMENT REGARDING FEDERALLY SPONSORED RESEARCH

This invention was made with government support under SBIR grant number R44CA213654 awarded by the National Cancer Institute of the National Institutes of Health. The government has certain rights in the invention.

FIELD OF THE DISCLOSURE

The present disclosure relates generally to the field of interstitial photodynamic therapy (I-PDT) and related methods and systems for treatment planning.

BACKGROUND

Photodynamic therapy (PDT) is a treatment to kill cancerous cells, diseased cells or harmful bacteria that involves therapeutic photo-chemical interaction of light, photosensitizer (PS) and oxygen within tumor cells, diseased cells or harmful bacteria (See e.g. MacDonald et. al., "Basic principles of photodynamic therapy," J. Nat. Cancer Inst. (1998) 90, 889-905; and Wilson et. al. "The physics of photodynamic therapy," Phys. Med. Biol. (1986) 31, 327-360.). In PDT, a PS is injected into the body or a PS prodrug is applied superficially and may accumulate at higher PS concentrations in diseased tissue compared to normal tissue. Ideally PDT will generate the reactive species only within the target volume, leading to damage of the tumor or diseased tissues, while minimizing damage to surrounding normal tissue. Unlike chemotherapy, PDT does not cause systemic toxicities, and unlike radiation therapy it does not cause cumulative damage in the local treatment area. It should be noted that PDT is used in many applications in addition to cancer, such as oral cavity disease, blood products purification, cardiovascular diseases, autoimmune diseases, bacterial or viral infections, eye diseases and skin diseases.

The numerous PDT applications are characterized by multiple geometries. Most can be classified as consisting of interstitial, surface (superficial) or intracavitary illumination. The use of interstitial illumination (I-PDT) using optical fibers for PDT includes prostate and head and neck cancers, among others. The use of surface illumination for PDT includes, but is not limited to, skin disease, skin cancer and bacterial or viral infections. The use of intracavitary illumination of the interior surface of a cavity for PDT includes, but is not limited to, applications such as oral cavity disease or cancer, disease or cancer of the gastrointestinal or respiratory tracts, thoracic cavity malignancies, bladder cancer and other cancers such as brain cancers where resection (removal) of primary tumors leaves a cavity. The ability of PDT to spare surrounding critical normal structures and better healing after treatment distinguish the benefit of PDT compared to other localized therapeutic approaches, such as surgical resection (excision) or tissue X-ray radiation.

While I-PDT has demonstrated strong clinical efficacy data in some cases, I-PDT treatment planning remains rudimentary for most clinical applications. Ideally, methods and systems for I-PDT treatment planning should be carried out via an established deterministic process which is based on the target region shape and properties and a sound computational model of the treatment. Conventionally, I-PDT treatment planning utilizes light dose (measured, for example, in $J/cm^2$) as the dosimetry parameter. However, such planning neglects many important treatment factors such as the concentration of the PS, the reaction kinetics of the PS resulting in PS photobleaching, the tissue optical properties, the initial oxygen concentration in the target region, the oxygen flow rate into the target region and the quantitative formation of the reactive oxygen species, denoted as ROS.

Singlet oxygen, $^1O_2$, is the primary cytotoxic ROS that is responsible for cell death in Type II PDT, although other ROS can also be involved in Type I PDT. In particular, conventional I-PDT treatment planning using light dose neglects these important factors that are needed and utilized in determining a much more accurate PDT-dose or a much more accurate reactive oxygen species dose, $[ROS]_{dose}$. PDT-dose, usually expressed in $\mu M \; J/cm^2$, for example, is defined as the time integral of the product of the fluence rate $\phi$ times the local PS concentration. $[ROS]_{dose}$ is the concentration of reactive oxygen species produced during treatment. PDT-dose and $[ROS]_{dose}$ also depend on the fluence rate (i.e., light fluence rate or light intensity or irradiance measured in $mW/cm^2$, for example) and the treatment time, which are additional treatment parameters. Inadequate treatment planning that does not take into account the concentration and photokinetics of the PS or the concentration and photokinetics of ROS can lead to increased rates of under- or over-treatment that manifest clinically as local recurrence of cancer or disease or unnecessary local cell death.

SUMMARY

The embodiments disclosed herein are proposed to address the issues with I-PDT disclosed herein. The proposed new and improved treatment planning methods and systems are accurate for any target region shape, various light transport parameters and various photokinetic parameters. Both PDT-dose and $[ROS]_{dose}$ depend on parameters such as PS photokinetic rate parameters, the initial PS concentration, PS photobleaching, tissue optical properties and changes in the tissue oxygen concentration during I-PDT. The embodiments of the present disclosure stem from the realization that prior art treatment planning methods that that calculate only light dose do not account for these parameters.

Some of the improved treatment planning methods and systems utilize, for example, Monte Carlo (MC) or Finite Element (FE) methods to initially calculate fluence rates for all portions of the target region, which is followed by photokinetic simulations to ensure that the entire target region receives a threshold PDT-dose or a threshold $[ROS]_{dose}$. It is also highly desirable to show treating physicians 2D or 3D visualizations of the resulting PDT-dose or $[ROS]_{dose}$, preferably showing, for example, 3D visualizations of the PDT-dose or $[ROS]_{dose}$ superimposed on 3D images of the target region as well as maps of the light fluence rate distribution. In particular, it is important to show the PDT-dose or $[ROS]_{dose}$ at the boundaries of the target region to ensure that all diseased or cancerous cells at the boundaries are treated with at least a threshold PDT-dose or a threshold $[ROS]_{dose}$.

Advantageously, the systems and methods described herein mitigate, alleviate or eliminate one or more deficiencies, disadvantages or issues in the art by providing optimization of treatment planning for interstitial photodynamic therapy.

Accordingly, in at least one embodiment, a method of administering interstitial photodynamic therapy by delivering treatment dose to a target region of a patient may include receiving, at a processor, information associated with the target region, an initial photo-sensitizer concentration, a plurality of initial photosensitizer photokinetic rate parameters, and a threshold treatment dose for a photosensitizer, the threshold treatment dose being a threshold photodynamic therapy-dose or a threshold reactive oxygen species dose. A location in the target region for inserting at least one interstitial treatment fiber to deliver the treatment light is determined. By the processor, initial values for therapeutic light power, and light emitting length and therapeutic treatment time are determined for the at least one interstitial treatment fiber. By the processor, computational spatial elements are determined for the target region and for the location of emitting surfaces of the at least one interstitial treatment fiber, and a fluence rate for delivering treatment light to each of the computational spatial elements. By the processor, a treatment dose is determined based on the fluence rate, the plurality of photosensitizer photokinetic rate parameters, and a photokinetic rate equation. By the processor, a command is generated for controlling a treatment light source to deliver the treatment dose to the target region via the at least one interstitial treatment fiber.

In accordance with at least one embodiment, a system for delivering a treatment dose to a target region of a patient for interstitial photodynamic therapy may include a treatment light source coupled to at least one interstitial treatment fiber. A diagnostic light source is coupled to at least one interstitial diagnostic fiber. At least one interstitial detector detects diagnostic light generated by the diagnostic light source and/or treatment light generated by the treatment light source and/or photosensitizer fluorescence generated by the diagnostic light source or the treatment light source. A processor is configured to receive information associated with the target region, an initial photosensitizer concentration, a plurality of initial photosensitizer photokinetic rate parameters, and a threshold treatment dose for a photosensitizer, the threshold treatment dose being a threshold photodynamic therapy-dose or a threshold reactive oxygen species dose. A location is determined in the target region for inserting the at least one interstitial treatment fiber to deliver the treatment light. Initial values are determined for therapeutic light power, and light emitting length and therapeutic treatment time for the at least one interstitial treatment fiber. Computational spatial elements are determined for the target region and for the location of emitting surfaces of the at least one interstitial treatment fiber, and a fluence rate for delivering treatment light to each of the computational spatial elements. A treatment dose is determined based on the fluence rate, the plurality of photosensitizer photokinetic rate parameters, and a photokinetic rate equation. A command is generated for controlling the treatment light source to deliver via the at least one interstitial treatment fiber the treatment dose to the target region.

In an aspect of the present application, a method of planning an interstitial photodynamic therapy treatment dose to be delivered to target region of a patient may include receiving, at a processor, information associated with the target region, an initial photo-sensitizer concentration, a plurality of initial photosensitizer photokinetic rate parameters, and a threshold treatment dose for a photosensitizer, the threshold treatment dose being a threshold photodynamic therapy-dose or a threshold reactive oxygen species dose. A location in the target region for inserting at least one interstitial treatment fiber to deliver the treatment light is determined. By the processor, initial values for therapeutic light power, and light emitting length and therapeutic treatment time are determined for the at least one interstitial treatment fiber. By the processor, computational spatial elements are determined for the target region and for the location of emitting surfaces of the at least one interstitial treatment fiber, and a fluence rate for delivering treatment light to each of the computational spatial elements. By the processor, a treatment dose is determined based on the fluence rate, the plurality of photosensitizer photokinetic rate parameters, and a photokinetic rate equation.

In accordance with at least one embodiment, a system for planning an interstitial photodynamic therapy may include a non-transitory computer-readable memory to store instructions and a processor to execute the instructions stored on the memory. The instructions cause the processor to receive information associated with the target region, an initial photosensitizer concentration, a plurality of initial photosensitizer photokinetic rate parameters, and a threshold treatment dose for a photosensitizer, the threshold treatment dose being a threshold photodynamic therapy-dose or a threshold reactive oxygen species dose. A location is determined in the target region for inserting the at least one interstitial treatment fiber to deliver the treatment light. Initial values are determined for therapeutic light power, and light emitting length and therapeutic treatment time for the at least one interstitial treatment fiber. Computational spatial elements are determined for the target region and for the location of emitting surfaces of the at least one interstitial treatment fiber, and a fluence rate for delivering treatment light to each of the computational spatial elements. A treatment dose is determined based on the fluence rate, the plurality of photosensitizer photokinetic rate parameters, and a photokinetic rate equation.

In accordance with at least one embodiment, a non-transitory machine-readable medium storing instructions to cause one or more processors to perform operations including receiving, at a processor, information associated with the target region, an initial photo-sensitizer concentration, a plurality of initial photosensitizer photokinetic rate parameters, and a threshold treatment dose for a photosensitizer, the threshold treatment dose being a threshold photodynamic therapy-dose or a threshold reactive oxygen species dose. A location in the target region for inserting at least one interstitial treatment fiber to deliver the treatment light is determined. By the processor, initial values for therapeutic light power, and light emitting length and therapeutic treatment time are determined for the at least one interstitial treatment fiber. By the processor, computational spatial elements are determined for the target region and for the location of emitting surfaces of the at least one interstitial treatment fiber, and a fluence rate for delivering treatment light to each of the computational spatial elements. By the processor, a treatment dose is determined based on the fluence rate, the plurality of photosensitizer photokinetic rate parameters, and a photokinetic rate equation.

Additional features and advantages of the subject technology will be set forth in the description below, and in part will be apparent from the description, or may be learned by practice of the subject technology. The advantages of the subject technology will be realized and attained by the structure particularly pointed out in the written description and embodiments hereof as well as the appended drawings.

It is to be understood that both the foregoing general description and the following detailed description are exemplary and explanatory and are intended to provide further explanation of the subject technology.

BRIEF DESCRIPTION OF THE DRAWINGS

Various features of illustrative embodiments of the present disclosure are described below with reference to the drawings. The illustrated embodiments are intended to illustrate, but not to limit, the present disclosure. The drawings contain the following figures.

DETAILED DESCRIPTION

Figure 1:
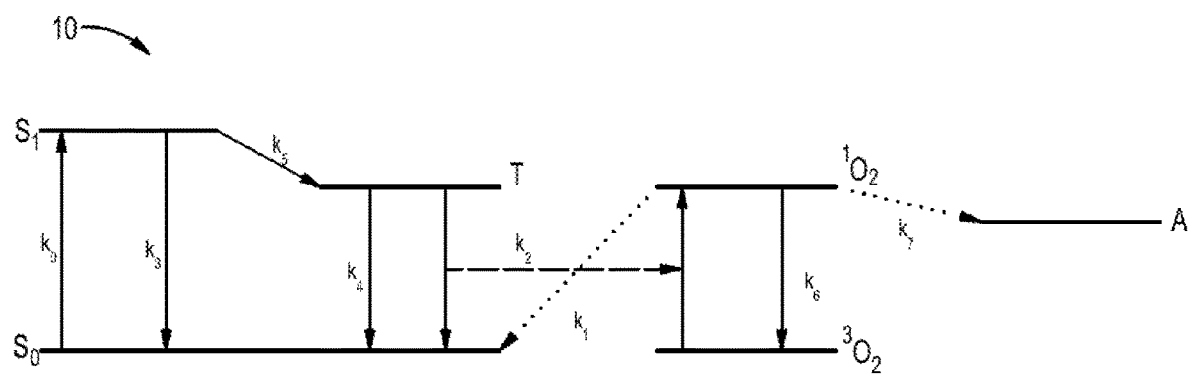
FIG. 1 is a Jablonski diagram for formation of singlet oxygen and the reaction of singlet oxygen with target cells and with the photosensitizer as in type II photodynamic therapy.

In the following detailed description, numerous specific details are set forth to provide a full understanding of the subject technology. It should be understood that the subject technology may be practiced without some of these specific details. In other instances, well-known structures and techniques have not been shown in detail so as not to obscure the subject technology.

Further, while the present description sets forth specific details of various embodiments, it will be appreciated that the description is illustrative only and should not be construed in any way as limiting. Furthermore, various applications of such embodiments and modifications thereto, which may occur to those who are skilled in the art, are also encompassed by the general concepts described herein.

PDT Dosimetry Overview

PDT dosimetry involves determining the treatment dose delivered to cancerous, diseased or normal tissue at a fixed or variable fluence rate, which is defined as the induced or delivered fluence rate (i.e., light intensity or irradiance in mW/cm$^2$) at each point in the target volume. There are three types of primary treatment dose metrics that are known to be used for PDT: (1) light dose (fluence) usually expressed in joules per centimeter squared (J/cm$^2$), for example, which is equal the fluence rate (mW/cm$^2$ or mJ/(s cm$^2$) times the time in seconds (s); (2) PDT-dose, usually expressed in μM J/cm$^2$, for example, which is defined as the time integral of the product of the local PS concentration times the fluence rate φ; and (3) reactive oxygen species dose, $[ROS]_{dose}$. For type II PDT, the reactive oxygen species dose, $[ROS]_{dose}$ is equal to the reactive singlet oxygen dose, $[^1O_2]_{dose}$. For each type of dose, a threshold dose is needed to kill cancer cells.

Light Dose

Standard PDT treatment planning of a treatment delivery protocol involves giving each patient the same total light dose (i.e. energy or incident fluence per area, J/cm$^2$), determined for a particular type of cancer, irrespective of variations of PS concentration or other variables within a single target region or variations among different patients. An example of a light dose is, for example, 100 J/cm$^2$, although other higher or lower light doses have been previously utilized. Depending on other conditions such as PS concentration and oxygen intake rate, the conventional light dose may or may not result in an effective PDT-dose or $[ROS]_{dose}$ or in an effective treatment. There is a threshold light dose needed to kill cells. This threshold can vary depending on treatment conditions such as the type of PS, the PS concentration, the initial oxygen concentration in the tissue, the oxygen flow rate delivered by blood flow to the tissue and the tissue optical properties. This variability in treatment conditions can lead to unreliable treatment results.

Some relevant surface PDT publications that include a threshold treatment light dose are: Sheng et. al. "Reactive oxygen species explicit dosimetry to predict local tumor control for Photofrin mediated photodynamic therapy," Proc. SPIE 10860, 108600V (2019); and Sheng et al., "Reactive oxygen species explicit dosimetry to predict tumor growth for benzoporphyrin derivative-mediated vascular photodynamic therapy", J. Biomedical Optics 25(6), 063805 (2020). An I-PDT publication for threshold light dose is Shafirstein et. al., "Irradiance controls photodynamic efficacy and tissue heating in experimental tumours: implication for interstitial PDT of locally advanced cancer", British Journal of Cancer, 19, 1191-1199 (2018). Some examples of threshold light dose for animals are listed in TABLE 1. It is expected that a threshold light dose is also needed for treating human cancer tissue. See, for example, Davidson et al., "Treatment planning and dose analysis for interstitial photodynamic therapy of prostate cancer," Phys. Med. Biol. 54 (2009) 2293-2313.

Without wishing to be bound by theory, the threshold doses may be reliable if the treated tissue has sufficient PS concentration and sufficient oxygen concentration (i.e. any oxygen concentration value above a threshold value that can kill target cells) to enable PDT. If the PS concentration or the oxygen concentration are too low, the target cancerous tissues may not be killed.

TABLE 1

| Photosensitizer | Animal | Threshold Light Dose [J/cm$^2$] |
|---|---|---|
| Photofrin | Mice | Approx. 100 (Sheng et. al., 2019) |
| | Mice | ≥45 (Shafirstein et. al., 2018) |
| | Rabbits | ≥45 (Shafirstein et. al., 2018) |
| BPD | Mice | Approx. 40 (vascular, Sheng et. al., 2020) |
| Tookcad | Human prostate | >23 (Davidson et.al., 2009) |

PDT-Dose

PDT-dose, usually expressed in µM J/cm$^2$, for example, is defined as the time integral of the product of the fluence rate $\phi$ times the local PS concentration. PDT-dose is usually more accurate for PDT treatment dosimetry than light dose because it takes into account the concentration of PS in the tissue, whereas light dose does not. For example, if the concentration of PS is very low or zero, no cancer will be killed even at a high light dose. Although PDT-dose will take the PS concentration into account, PDT-dose does not take into account the local oxygen concentration. If the oxygen concentration is too low, cancer cells will not be killed even for a high PDT-dose. There is a threshold PDT-dose needed to kill cells. This threshold can vary depending on conditions such as the type of PS, the PS concentration, the initial oxygen concentration in the tissue, the oxygen flow rate delivered by blood flow to the tissue and the tissue optical properties. Some relevant surface PDT publications that include a threshold PDT-dose are: Kim, et al; "Evaluation of singlet oxygen explicit dosimetry for predicting treatment outcomes of benzoporphyrin derivative monoacid ring A-mediated photodynamic therapy"; J Biomedical Optics, 22(2), 028002 (2017); Penjweini et al; "Evaluation of the 2-(1-Hexyloxyethyl)-2-devinyl pyropheophorbide (HPPH) mediated photodynamic therapy by macroscopic singlet oxygen modeling"; J. Biophotonics 9(11-12), 1344-1354 (2016); Sheng et. al. "Reactive oxygen species explicit dosimetry to predict local tumor control for Photofrin mediated photodynamic therapy," Proc. SPIE 10860, 108600V (2019); Sheng, T et al; "Reactive oxygen species explicit dosimetry to predict tumor growth for benzoporphyrin derivative-mediated vascular photodynamic therapy", J. Biomedical Optics 25(6), 063805 (2020)

Some surface PDT examples of threshold PDT-dose for animals are listed in TABLE 2. It is expected that a threshold PDT-dose is also needed for treating human cancer tissue. The threshold doses are only reliable if the treated tissue has sufficient oxygen concentration to enable PDT.

TABLE 2

| Photosensitizer | Animal | Threshold PDT-dose (µM J/cm$^2$) |
|---|---|---|
| Photofrin | Mice | 439 (Sheng et. al., 2019) |
| BPD | Mice | 58 ± 12 (Kim et. al., 2017) |
| | | 7.5 (vascular, Sheng et. al., 2020) |
| HPPH | Mice | 52.62 ± 14.9 (Penjweini et. al., 2016) |

Reactive Oxygen Species Dose, $[ROS]_{dose}$, or Reactive Singlet Oxygen Dose, $[^1O_2]_{dose}$ Recent experimental surface PDT work on tumors in mice indicates that the reactive oxygen species treatment dose, $[ROS]_{dose}$, or, in particular, the reactive singlet oxygen dose, $[^1O_2]_{dose}$, generated by the treatment light is more important than the conventional total light dose. See for example: Sheng, T. et al; "Reactive oxygen species explicit dosimetry to predict tumor growth for benzoporphyrin derivative-mediated vascular photodynamic therapy", J. Biomedical Optics 25(6), 063805 (2020); Penjweini, R. et al; "Evaluation of the 2-(1-Hexyloxyethyl)-2-devinyl pyropheophorbide (HPPH) mediated photodynamic therapy by macroscopic singlet oxygen modeling"; J. Biophotonics 9(11-12), 1344-1354 (2016) and Penjweini, R. et. al.; In-vivo outcome study of HPPH medicated PDT using singlet oxygen explicit dosimetry (SOED), Proc. of SPIE 2015; Vol. 9308, 93080N. The same light dose may result in differing amounts of generated singlet oxygen or other ROS depending on the treatment conditions such as the fluence rate and oxygen intake from blood flow. It has been found in mice that a threshold $[ROS]_{dose}$ should be reached during PDT treatment to successfully kill cancer cells. See, for example, Sheng et al, "Reactive oxygen species explicit dosimetry to predict tumor growth for benzoporphyrin derivative-mediated vascular photodynamic therapy", J. Biomedical Optics 25(6), 063805 (2020). It is expected that a threshold $[ROS]_{dose}$ or, in particular, a threshold $[^1O_2]_{dose}$ will also be required to kill cancer cells in humans. This assumption cannot be directly tested since the experiments that were done on mice cannot be done on humans. The singlet oxygen threshold dose needed to kill cancer will depend on the type of tumor undergoing the treatment. Superficial PDT examples of threshold $[^1O_2]_{dose}$ are shown in TABLE 3, where the data are taken from (a) Zhu et. al; "In-vivo singlet oxygen threshold doses for PDT"; Photon Lasers Med. 2015; 4(1), 59-71; (b) Qiu et al; "Macroscopic singlet oxygen modeling for dosimetry of Photofrin-mediated photodynamic therapy: an in-vivo study"; J. Biomedical Optics, 21(8), 088002 (2016); (c) Kim et al; "Evaluation of singlet oxygen explicit dosimetry for predicting treatment outcomes of benzoporphyrin derivative monoacid ring A-mediated photodynamic therapy"; J Biomedical Optics, 22(2), 028002 (2017); (d) Penjweini et al; "Evaluation of the 2-(1-Hexyloxyethyl)-2-devinyl pyropheophorbide (HPPH) mediated photodynamic therapy by macroscopic singlet oxygen modeling"; J. Biophotonics 9(11-12), 1344-1354 (2016). Note that the values of threshold $[^1O_2]_{dose}$ in TABLE 3 are labeled $[O_2]_{rx}$ in the publications.

TABLE 3

| Photosensitizer | Animal | Threshold $[^1O_2]_{dose}$ (mM) |
|---|---|---|
| Photofrin | Mice | 0.56 ± 0.26 (Zhu et. al., 2015) |
| | | >1.0 (Qiu et. al., 2016) |
| BPD | Mice | 0.72 ± 0.21 (Zhu et. al., 2015) |
| | | 0.98 ± 012 (Kim et. al. 2017) |
| HPPH | Mice | 0.98 ± 0.11 (Penjweini et. al., 2016) |

Fluence Rate as a Secondary Dose Metric

In the case of using light dose as the primary metric, it has been found that a secondary dose metric is also necessary. It was found that a threshold fluence dose rate $\phi_T$ (i.e. threshold irradiance in, for example, mW/cm$^2$) is necessary to kill cancer in mice and rabbits. Shafirstein et. al., "Irradiance controls photodynamic efficacy and tissue heating in experimental tumours: implication for interstitial PDT of locally advanced cancer", British Journal of Cancer, 19, 1191-1199

(2018). In particular, healing threshold fluence rates (see TABLE 4) have been shown for I-PDT treatment of mice and rabbits using the light dose as the dose metric.

TABLE 4

| Photosensitizer | Animal | Threshold Fluence Rate $\phi_T$ [mW/cm$^2$] |
|---|---|---|
| Photofrin | Mice | 8.4 (Shafirstein et. al., 2018) |
|  | Rabbits | 16.5 (Shafirstein et. al., 2018) |

PDT Treatment Planning

In order to do accurate dosimetry in treatment planning and treatment delivery, computer simulations are performed. For superficial PDT and intracavitary PDT only, there exist prior art computer devices and software that can calculate PDT-dose, $[^1O_2]_{dose}$ and PDT treatment fluence rates, but only for a single fixed treatment light source position. To our knowledge, there are no prior art computer devices and software for I-PDT that utilize photokinetic simulations to calculate PDT-dose or reactive oxygen species dose, $[ROS]_{dose}$, with one or more light sources.

Input parameters include the treatment light source fluence rate $\phi$, the target shape, the light source position relative to target shape, the optical parameters of the target and the PS concentration. Prior art computer devices and software for surface PDT are described in Beeson et. al., "Validation of combined Monte Carlo and photokinetic simulations for the outcome correlation analysis of benzoporphyrin derivative-mediated photodynamic therapy on mice," J. Biomed. Opt 24(3), 035006, (2019a), and Beeson et. al. "Validation of Dosie™ combined Monte Carlo and photokinetic simulations for the analysis of HPPH-mediated photodynamic therapy on mice," Proc. SPIE 10860, 108600N (2019b). These publications describe Monte Carlo simulations to determine light dose and treatment fluence rates and photokinetic simulations that use the fluence rate simulations to determine PDT-dose and $[^1O_2]_{dose}$. An example of photokinetic simulations to determine $[^1O_2]_{dose}$ follows.

The amount of singlet oxygen $[^1O_2]$ generated during PDT depends on the PS concentration and other parameters such as the amount of oxygen in the affected tissue, the amount of new oxygen that is being supplied to the tissue by blood vessels—the oxygen intake rate—the fluence rate (mW/cm$^2$) at the location of the PDT treatment and the treatment time. Note that a given threshold amount of singlet oxygen to kill cancer cells can be generated by a wide range of fluence rates and treatment times.

In order to calculate the amount of singlet oxygen generated for either superficial PDT or intracavitary PDT at any point within cancerous tissue or on its surface, one must consider two coupled calculations: (1) light transport through the tissue initiated by a given fluence rate incident to the surface of the tumor tissue (also called direct light), where the delivered light inside the tissue has a different fluence rate after undergoing scattering and absorption by the tissue; and (2) the photokinetics of the PS interacting with the delivered light, where the interaction depends on the fluence rate of the delivered light.

The light transport portion of the calculation can be addressed by, for example, Monte Carlo or finite element (FE) simulations or by approximate solutions to the diffusion equation. Monte Carlo (MC) methods are a set of randomized computational algorithms particularly suitable for simulations of complex systems. Distinct from most deterministic numerical techniques which produce solutions by solving a set of differential equations, Monte Carlo methods generate solutions by estimating the probability distribution after launching a large number of independent random trials. (See, for example, Fang et. al., "Monte Carlo simulation of photon migration in 3D turbid media accelerated by graphics processing units," Optics Express 17(22), 20178 (2009), Beeson et. al., "Validation of combined Monte Carlo and photokinetic simulations for the outcome correlation analysis of benzoporphyrin derivative-mediated photodynamic therapy on mice," J. Biomed. Opt 24(3), 035006 (2019a), and Beeson et. al. "Validation of Dosie™ combined Monte Carlo and photokinetic simulations for the analysis of HPPH-mediated photodynamic therapy on mice," Proc. SPIE 10860, 108600N (2019b).) In contrast to MC methods, FE can be used to solve the time-dependent light diffusion approximation equation as a boundary value problem with appropriate initial conditions. See, for example, Oakley et al., "A New Finite Element Approach for Near Real-Time Simulation of Light Propagation in Locally Advanced Head and Neck Tumors Lasers," Lasers in Surgery and Medicine 47, 60-67 (2015).

One can calculate the total amount of singlet oxygen generated by a PDT treatment by solving numerically the explicit kinetic rate equations of the PDT photo-chemical reactions. FIG. 1 shows Jablonski diagram 10 for Type II PDT where single-photon photo-excitation of a photosensitizer (PS) from the ground state $S_0$ to the excited state $S_1$ results in the formation of singlet oxygen, $^1O_2$, from ground state triplet oxygen, $^3O_2$. The singlet oxygen then can react and destroy cancer target cells, denoted as A, as well as react and destroy a portion of the PS ground state $S_0$. See e.g. Wang et. al; Explicit dosimetry for photodynamic therapy: macroscopic singlet oxygen modeling, J. Biophotonics 2010 June; 3(5-6); 304-318). The reactions for Type II PDT can be described by the following set of coupled differential equations (1)-(6). (For Type I PDT, the same set of equations can also be used or different Jablonski diagram with an alternative set of equations can optionally be substituted. See, for example Kim et. al.; On the in vivo photochemical rate parameters for PDT reactive oxygen species modeling, Phys. Med. Biol. 62 (2017) R1-R48.)

In the following equations for Type II PDT, the concentration of the ground state of the PS is $[S_0]$, the concentration of the first excited state of the PS is $[S_1]$, the concentration of the triplet state of the PS is $[T]$, the concentration of the ground state of oxygen is $[^3O_2]$, the concentration of the excited state of oxygen is $[^1O_2]$, and the concentration of the cancer target is $[A]$. The photo-kinetic parameters $k_0$-$k_7$, g, $\delta$, and $S_\Delta$ are defined in TABLE 5.

$$\frac{d[S_o]}{dt} = -k_0[S_o] - k_1[^1O_2]([S_0]+\delta) + k_2[T][^3O_2] + k_3[S_1] + k_4[T] \quad (1)$$

$$\frac{d[S_1]}{dt} = (k_3+k_5)[S_1] + k_0[S_0] \quad (2)$$

$$\frac{d[T]}{dt} = -k_2[T][^3O_2] + k_4[T] + k_5[S_1] \quad (3)$$

$$\frac{d[^3O_2]}{dt} = -S_\Delta k_2[T][^3O_2] + k_6[^1O_2] + g \quad (4)$$

$$\frac{d[^1O_2]}{dt} = -k_1([S_0]+\delta)[^1O_2] + S_\Delta k_2[T][^3O_2] - k_6[^1O_2] - k_7[A][^1O_2] \quad (5)$$

$$\frac{d[A]}{dt} = -k_7[A][^1O_2] \quad (6)$$

The system of differential equations (1)-(6) can be solved numerically (See e. g. Zhu et. al; Macroscopic modeling of the singlet oxygen production during PDT; Proc. SPIE 2007; Vol. 6427, 642708; and Potasek et. al.; Calculation of singlet oxygen formation from one photon absorbing photosensitizers used in PDT; Proc. SPIE 2013; Vol. 8568, 85681D). However, there are two issues here. First, the rate parameters, $k_0$-$k_7$, may not be accurately known for a photosensitizer in living tissue. Second, since the treatment time scales for the reactions in Equations (1)-(6) range from nanoseconds to thousands of seconds, numerical calculations can take hours to complete which is undesirable for treatment planning.

To get around these issues, approximate solutions to Equations (1)-(6) have been described. (See e.g. Wang et. al; Explicit dosimetry for photodynamic therapy: macroscopic singlet oxygen modeling, J. Biophotonics 2010 June; 3(5-6), 304-318) Since the lifetimes of $[S_1]$, $[T]$ and $[^1O_2]$ are short compared to $[S_0]$ and $[^3O_2]$, then $[S_1]$, $[T]$ and $[^1O_2]$ are treated as reaching steady state relative to $[S_0]$ and $[^3O_2]$. The derivatives in equations (2), (3) and (5) are set equal to zero as shown in equations (7), (8) and (9).

$$\frac{d[S_1]}{dt} = 0 \quad (7)$$

$$\frac{d[T]}{dt} = 0 \quad (8)$$

$$\frac{d[^1O_2]}{dt} = 0 \quad (9)$$

As explained in e.g. Wang et. al; Explicit dosimetry for photodynamic therapy: macroscopic singlet oxygen modeling, J. Biophotonics 2010 June; 3(5-6), 304-318, the six Equations (1)-(6) then reduce to the following three Equations (10)-(12). One can solve the system of Equations (10)-(12) numerically and determine the total singlet oxygen dose, $[^1O_2]_{dose}$, which is denoted in Wang, K. K. et. al. publication as $[^1O_2]_{rx}$, for Type II PS. Or one can solve for $[ROS]_{dose}$ using the equivalent set of equations as described in Sheng et. al.; Reactive oxygen species explicit dosimetry to predict tumor growth for benzoporphyrin derivative-mediated vascular photodynamic therapy, J. Biomed. Opt. 2020; 25(6), 063805 for Type I PS. For simplicity, it can be assumed that the constant $S_\Delta = 0$.

$$\frac{d[S_0]}{dt} = -\frac{[^3O_2]}{[^3O_2]+\beta}([S_0]+\delta)\phi[S_0]\xi\sigma \quad (10)$$

$$\frac{d[^3O_2]}{dt} = -\frac{[^3O_2]}{[^3O_2]+\beta}\phi[S_0]\xi + g\left(1 - \frac{[^3O_2]}{[^3O_2]_0}\right) \quad (11)$$

$$\frac{d[ROS]_{dose}}{dt} = \xi\frac{[^3O_2]}{[^3O_2]+\beta}\phi[S_0] \quad (12)$$

The total singlet oxygen dose can be found by integrating Equation (12) from time t=0 to the treatment time, T, which gives:

$$[ROS]_{dose} = \int_0^T \xi\frac{[^3O_2]}{[^3O_2]+\beta}\phi[S_0]dt \quad (13)$$

The parameters used in Equations (10)-(13) are defined in TABLE 5. The $\xi$, $\sigma$ and $\beta$ parameters are related to the rates $k_1$-$k_7$ and $[A]$. The $\xi$, $\sigma$ and $\beta$ parameters can differ for different photosensitizers and can be determined experimentally. The fluence rate is denoted as $\phi$. Equations (10)-(13) can be (13) solved by standard numerical integration techniques (e.g., Runge-Kutta method) when the starting values of the PS concentration, $[S_0 (t=0)]$, the tissue oxygen concentration, $[^3O_2 (t=0)]$, and the oxygen intake rate, g, are specified. A table of kinetic parameters for a variety of photosensitizers can be found in Kim et. al.; On the in vivo photochemical rate parameters for PDT reactive oxygen species modeling, Phys. Med. Biol. 62 (2017) R1-R48.

TABLE 5

| Parameter | Definition | Units |
|---|---|---|
| $k_0$ | Photon absorption rate of PS per PS concentration | $s^{-1}$ |
| $k_1$ | Bimolecular rate for $^1O_2$ reaction with PS ground state $S_0$ | $s^{-1}\mu M^{-1}$ |
| $k_2$ | Bimolecular rate of PS triplet T state quenching by $^3O_2$ | $s^{-1}\mu M^{-1}$ |
| $k_3$ | Decay rate of PS first excited state $S_1$ | $s^{-1}$ |
| $k_4$ | Rate of decay of PS triplet state T | $s^{-1}$ |
| $k_5$ | Decay rate of PS first excited state $S_1$ to triplet state T | $s^{-1}$ |
| $k_6$ | $^1O_2$ to $^3O_2$ decay rate | $s^{-1}$ |
| $k_7$ | Bimolecular rate of reaction of $^1O_2$ with cancer target A | $s^{-1}\mu M^{-1}$ |
| $S_\Delta$ | Fraction of PS triplet state T to $^3O_2$ reactions to produce $^1O_2$ | — |
| $\delta$ | Low concentration correction | $\mu M$ |
| g | $^3O_2$ oxygen intake rate | $\mu M s^{-1}$ |
| $\xi$ | $S_\Delta\left(\frac{k_5}{k_5+k_3}\right)\frac{\varepsilon}{hv}\left(\frac{k_7[A]/k_6}{k_7[A]/k_6+1}\right)$ | $cm^2 mW^{-1} s^{-1}$ |
| $\sigma$ | $k_1/(k_7[A])$ | $\mu M^{-1}$ |
| $\varepsilon$ | PS extinction coefficient | $cm^{-1}\mu M^{-1}$ |
| hv | Energy of one photon; h is Planck's constant; v is the photon frequency | Joules |
| $\beta$ | $k_4/k_2$ | $\mu M$ |
| $\phi$ | Fluence rate | $mW/cm^2$ |
| $[S_0 (t=0)]$ | Initial PS concentration at time t = 0 | $\mu M$ |
| $[^3O_2 (t=0)]$ | Initial ground state oxygen concentration at time t = 0 | $\mu M$ |

Some experimentally determined values for the $\varepsilon$, $\xi$ and $\beta$ parameters for different photosensitizers are listed in TABLE 6. (See e. g. Zhu et. al; In-vivo singlet oxygen threshold doses for PDT; Photon Lasers Med. 2015; 4(1), 59-71 and Ong et al, Reactive oxygen species explicit dosimetry (ROSED) of type I photosensitizer; Proc. SPIE: 2018, 10476, 1-10.)

TABLE 6

| Parameter (units) | Photosensitizer (wavelength) |
|---|---|
| $\varepsilon$ ($cm^{-1}\mu M^{-1}$) | Photofrin (630 nm): 0.0035 |
| | mTHPC (650 nm): 0.048 |
| | BPD (690 nm): 0.0783 |
| | Tookad (762 nm) |
| $\xi$ ($cm^2 mW^{-1} s^{-1}$) | Photofrin: $3.7 \times 10^{-3}$ |
| | mTHPC: $30.0 \times 10^{-3}$ |
| | BPD: $51.0 \times 10^{-3}$ |
| | Tookad: $122 \times 10^{-3}$ |
| $\sigma$ ($\mu M^{-1}$) | Photofrin: $7.6 \times 10^{-5}$ |
| | mTHPC: $2.97 \times 10^{-5}$ |
| | BPD: $1.7 \times 10^{-5}$ |
| | Tookad: $2.6 \times 10^{-5}$ |

TABLE 6-continued

| Parameter (units) | Photosensitizer (wavelength) |
|---|---|
| β (μM) | Photofrin: 11.9 |
| | mTHPC: 8.7 |
| | BPD: 11.9 |
| | Tookad: 11.9 |

The kinetic Equations (10)-(13) are also needed in order to calculate PDT-dose. To calculate PDT-dose, which is defined as the time integral of the product of the fluence rate ϕ times the local PS concentration, one can solve Equation (10) for the PS concentration (i.e. [$S_0$] in Equation (10)) as a function of time, multiply by the fluence rate ϕ and then calculate the time integral of the result.

Referring now to FIG. 1, which shows Jablonski diagram 10 for single-photon, photo-excitation of an electron of a photosensitizer (PS) from a ground state $S_0$ to an excited state $S_1$, transferring an electron to a triplet state T which undergoes energy transfer from state T to oxygen resulting in the formation of singlet oxygen, $^1O_2$, from ground state triplet oxygen, $^3O_2$. The singlet oxygen then can react and destroy cancer target cells, denoted as A, as well as react and destroy a portion of the PS ground state, which is labeled $S_0$.

Figure 2:
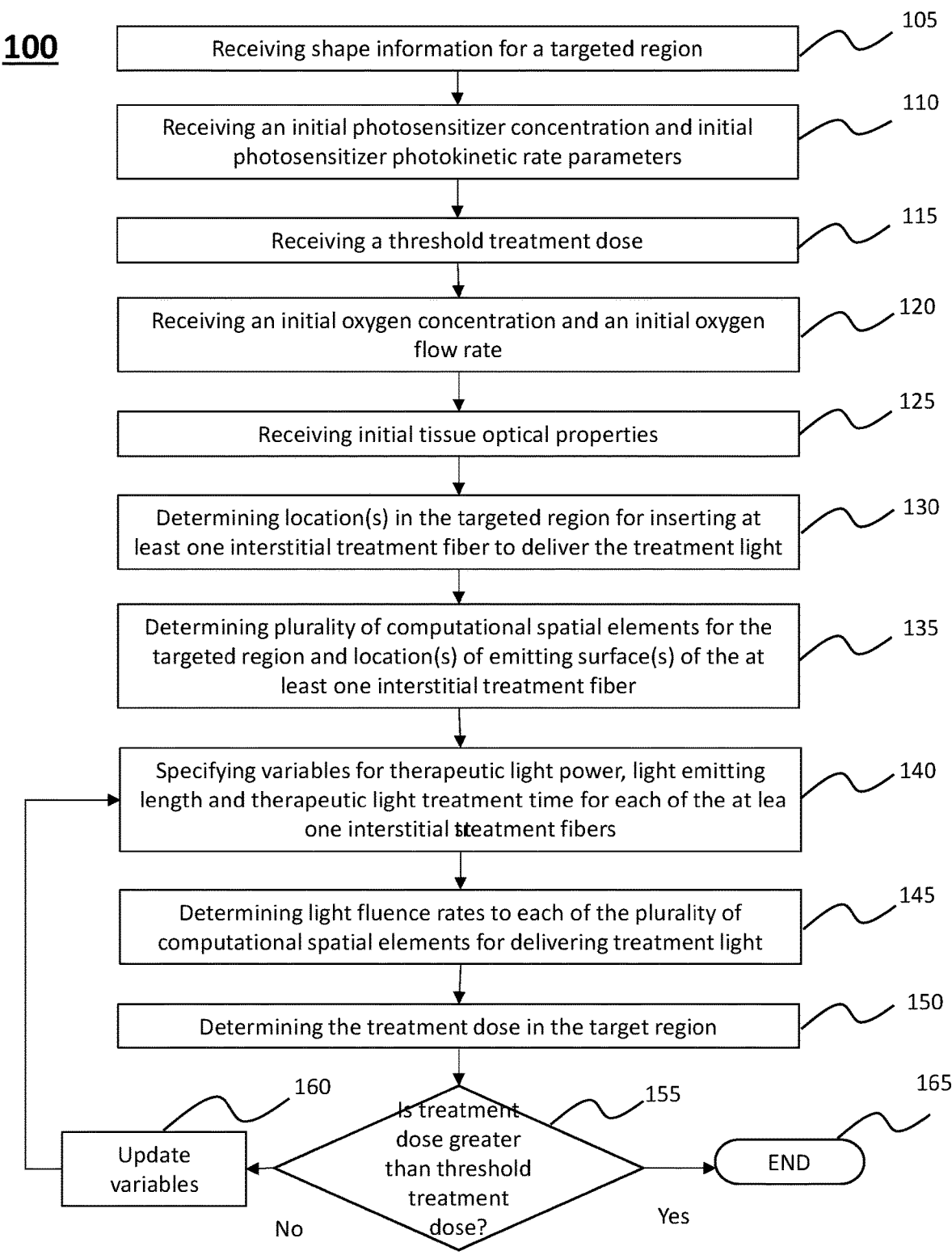
FIG. 2 schematically depicts a method for generating an interstitial photodynamic therapy plan.

The present disclosure, thus, provides a method for generating an interstitial photodynamic therapy treatment plan. FIG. 2 depicts an embodiment of the method 100 for treatment planning for optimizing I-PDT treatment dose delivery to a target region. Advantageously, the method 100 establishes a treatment plan that will deliver at least a threshold treatment dose over the entire target region and that is also within an acceptable tolerance that will not significantly damage healthy tissue and organs-at-risk. The threshold treatment dose can be a threshold PDT-dose, a threshold [ROS]$_{dose}$ or a threshold light dose. Preferably the threshold treatment dose is a threshold PDT-dose or a threshold [ROS]$_{dose}$. The threshold [ROS]$_{dose}$ may be a threshold [$^1O_2$]$_{dose}$. It is more preferable that each treatment utilizing a primary threshold PDT-dose or primary threshold [ROS]$_{dose}$ optionally adds a secondary dose metric, where the secondary dose metric is a threshold fluence rate ϕ needed in order to kill cancer cells or where the secondary dose metric is a threshold light dose.

In some embodiments, the method 100 utilizes a computer processor that receives input information for the treatment plan and determines a therapeutic dose for a target region in a patient.

At 105, a computer processor receives shape information for the target region. The shape of the target region may be obtained using imaging techniques including, but not limited to, a computed tomography (CT) scan, a positron emission tomography (PET) scan, a magnetic resonance imaging (MRI) scan, an ultrasound image or a 3D camera image. CT scans and MRI scans, for example, provide slice information about a 3D target region such as a tumor. Using commercially-available or open-source geometry processing software packages, one can take the slice information, manually or automatically outline the target region in each slice, and then construct a 3D representation of the target region.

At 110, the computer processor receives an initial photosensitizer concentration and initial photosensitizer photokinetic rate parameters. The photosensitizer photokinetic rate parameters will be different for different photosensitizers. A table of photokinetic rate parameters for a variety of photosensitizers can be found, e.g., in Kim et. al.; On the in vivo photochemical rate parameters for PDT reactive oxygen species modeling, Phys. Med. Biol. 62 (2017) R1-R48.

At 115, the computer processor receives threshold treatment dose information for the target region. Preferably, the primary threshold treatment dose metric is a threshold PDT-dose or a threshold [ROS]$_{dose}$. The threshold [ROS]$_{dose}$ may be a threshold [$^1O_2$]$_{dose}$. The threshold PDT-dose or the threshold [ROS]$_{dose}$ may be obtained from prior clinical data or from published or unpublished results. It is preferable that each treatment utilizing a primary threshold PDT-dose or primary threshold [ROS]$_{dose}$ optionally adds a secondary dose metric, where the secondary dose metric is a threshold fluence rate ϕ needed in order to kill cancer cells or where the secondary dose metric is a threshold light dose.

The threshold treatment dose can be delivered by all of the interstitial treatment fibers simultaneously to the entire target region or delivered sequentially (incremental treatment dose) in time by smaller sub-groups of the fibers to portions of the target region. Preferably, an incremental treatment dose to a portion of the target region from a sub-group of one or more interstitial treatment fibers (that is part of the larger total number of interstitial treatment fibers) is included in the treatment dose only when the fluence rate to the portion of the target region from the sub-group is equal to or greater than a threshold fluence rate. Whether the threshold treatment dose is delivered simultaneously to the entire target region or delivered sequentially in time to portions of the target region, at the end of the treatment every elementary volume of the target region should preferably receive at least a threshold treatment dose at a threshold fluence rate or higher.

At 120, the computer processor receives an initial oxygen concentration for the target region and an initial oxygen flow rate into the target region. The initial oxygen concentration and the initial oxygen flow rate can be determined by measurements taken on the target region of the patient. Oxygen concentration can be measured with, for example but not limited to, an OxyLite Pro oxygen monitor (Oxford Optronix, Oxford, UK) and blood flow rate (proportional to oxygen flow rate) can be determined, for example, by diffuse correlation spectroscopy. For both types of measurements, see Ong et. al.; Reactive oxygen species explicit dosimetry for Photofrin-mediated pleural photodynamic therapy, Photochem Photobiol. 2020; 96: 340-348. If measurement results are not available, data from published or unpublished results may be substituted.

At 125, the computer processor receives initial tissue optical properties for the target region. Tissue optical properties can be determined by measurements taken on the target region of the patient. The tissue optical properties comprise the light absorption parameter, mua (or $\mu_a$) the light scattering parameter, mus (or $\mu_s$), the scattering anisotropy factor, $g_s$, and the index of refraction, n. Note that the scattering anisotropy factor, $g_s$, is a different parameter than the photokinetic parameter, g, for the oxygen intake rate. The optical properties $\mu_a$ and $\mu_s$ may be measured, for example, by broadband reflectance spectroscopy (Finlay et. al., Diffuse reflectance spectra measured in vivo in human tissues during Photofrin-mediated pleural photodynamic therapy, Proc SPIE Int Soc Opt Eng. 2006, 6139). If measurement results are not available, data from published or unpublished results may be substituted. The tissue optical properties used in simulations of the threshold treatment dose may be different for each material (e.g. target region, healthy tissue, air).

At 130, one or more locations in the target region for inserting one or more interstitial treatment fibers to deliver the treatment light are determined, either manually or by the computer processor. Preferably the interstitial treatment fibers are surrounded by light-transparent catheters. Light-transparent catheters are commercially available from vendors such as, for example, Best Medical International, Inc., Springfield, Va. The interstitial treatment fibers may be non-diffusing optical fibers or preferably, diffusing optical fibers. Diffusing optical fibers can be obtained from vendors such as, for example, Medlight S.A., Switzerland. Standard diffuser lengths are 10, 15, 20, 25, 30, 40, 50, 70 mm.

Manual means for determining locations of interstitial treatment fibers include letting the treating clinician decide on the positions of the interstitial treatment fibers. This may be required if there are treatment-sensitive organs-at-risk near the target region. In any case, the treating clinician makes the final decision on the position of the interstitial treatment fibers. Another option for determining locations of interstitial treatment fibers is to use a standard brachytherapy transperineal implant template, which has a rectangular array of holes with 5 mm center-to-center separation that can be used to position light-transmitting catheters and interstitial treatment fibers in a regular or non-regular array. Once the positions of the one or more interstitial treatment fibers have been determined, one can use any geometry processing software to create cylindrical holes into the computer-generated 3D shape of the target region where the interstitial treatment fibers will be located.

At 135, a plurality of computational spatial elements for the target region and for the location(s) of the emitting surface(s) of at least one interstitial treatment fiber are determined. Simulations of the treatment light dose and fluence rate can be done by Monte Carlo (MC) methods or Finite Element (FE) methods. Voxel elements or tetrahedral mesh elements can be used as the computational spatial elements for MC simulation. Tetrahedral mesh elements can be chosen as computational spatial elements for FE numerical calculations.

At 140, the three initial variables for the treatment plan parameters are specified: therapeutic light power, light emitting length and therapeutic light treatment time, for each at least one interstitial treatment fiber. This can be done by manual means or by automatic or semi-automatic optimization means. Therapeutic light power is the total light power directed into the entire light emitting length of the interstitial treatment fiber and is expressed, for example, in units of milliwatts (mW). Alternatively, in many I-PDT publications, therapeutic light power is defined as light power per unit length of the entire light emitting length expressed, for example, in milliwatts per centimeter (mW/cm) of light emitting length.

At 145, the fluence rates to each of the plurality of computational spatial elements for delivering the treatment light are determined. This is done prior to using the photokinetic rate equations and the photosensitizer photokinetic rate parameters to calculate the treatment dose. The calculations can be done using either MC or FE methods.

At 150, the treatment dose to the interior volume of the target region is determined. The fluence rates calculated at 145 for each of the plurality of computational spatial elements as well as the photokinetic rate equations and the photosensitizer photokinetic rate parameters are used for determining the treatment dose to the interior volume of the target region. Additionally or optionally, the treatment dose to the boundary of the target region for each of the plurality of computational spatial elements may also be determined at 150.

At 155, it is determined whether the treatment dose is greater than threshold treatment dose. Note that the threshold treatment dose is defined at 115. Preferably the threshold treatment dose is a threshold PDT-dose or a threshold $[ROS]_{dose}$. The threshold $[ROS]_{dose}$ may be a threshold $[^1O_2]_{dose}$. It is more preferable that each treatment utilizing a primary threshold PDT-dose or primary threshold $[ROS]_{dose}$ optionally adds a secondary dose metric, where the secondary dose metric is a threshold fluence rate $\phi$ needed in order to kill cancer cells or where the secondary dose metric is a threshold light dose. For effective treatment, it is preferred that the treatment dose is greater than the threshold treatment dose for at least 80 percent of the computational spatial elements of the interior volume of the target region and optionally for at least 80 percent of the computational spatial elements of the boundary of the target region. More preferably the treatment dose is greater than the threshold treatment dose for at least 90 percent of the computational spatial elements of the interior volume of the target region and optionally for at least 90 percent of the computational spatial elements of the boundary of the target region. Most preferably the treatment dose is greater than the threshold treatment dose for all or substantial all of the computational spatial elements of the interior volume of the target region and optionally for all or substantially all of the computational spatial elements of the boundary of the target region.

If the answer is 'No', at 160, the three variables (therapeutic light power, light emitting length and therapeutic light treatment time) for each at least one interstitial treatment fiber are updated and the method 100 returns to 140. 140, 145, 150 and 155 are then repeated until the treatment dose is greater than the threshold treatment dose in the preferred percent of the target region. Note that increasing the therapeutic light power increases the fluence rate.

If the answer is 'Yes', at 165, the simulation is terminated.

Optimization means for Steps 140 to 165 may be done by optimization software that may include, but is not limited to, Cimmino's method as disclosed in U.S. Pat. No. 8,986,358 and convex optimization (Yassine et al., "Automatic interstitial photodynamic therapy planning via convex optimization," Biomedical Optics Express, Vol. 9, No. 2 (1 Feb. 2018)).

Additional features can be added to the method 100 as illustrated in FIG. 2. The steps described in FIG. 2 are usually done after the shape of the target region has been obtained by means including, but not limited to, a computed tomography (CT) scan, a positron emission tomography (PET) scan, a magnetic resonance imaging (MRI) scan, an ultrasound image or a 3D camera image, but before a clinician begins treatment.

Once a clinician inserts interstitial treatment fibers into the target region, the clinician may find that the locations of the interstitial treatment fibers are different than in the initial treatment plan. The interstitial photodynamic therapy treatment plan parameters should be updated to take into account the change(s) in the location(s) of the at least one interstitial treatment fiber for the target region that have occurred since the interstitial photodynamic therapy treatment plan was first generated. In addition, the interstitial photodynamic therapy treatment plan may need to be updated before or during the treatment if there are measurements showing changes for the target region in at least one of the initial photosensitizer concentration, the plurality of initial photosensitizer photokinetic rate parameters, the initial tissue oxygen concentration, the initial tissue optical properties or the initial oxygen flow rate.

Figure 3:
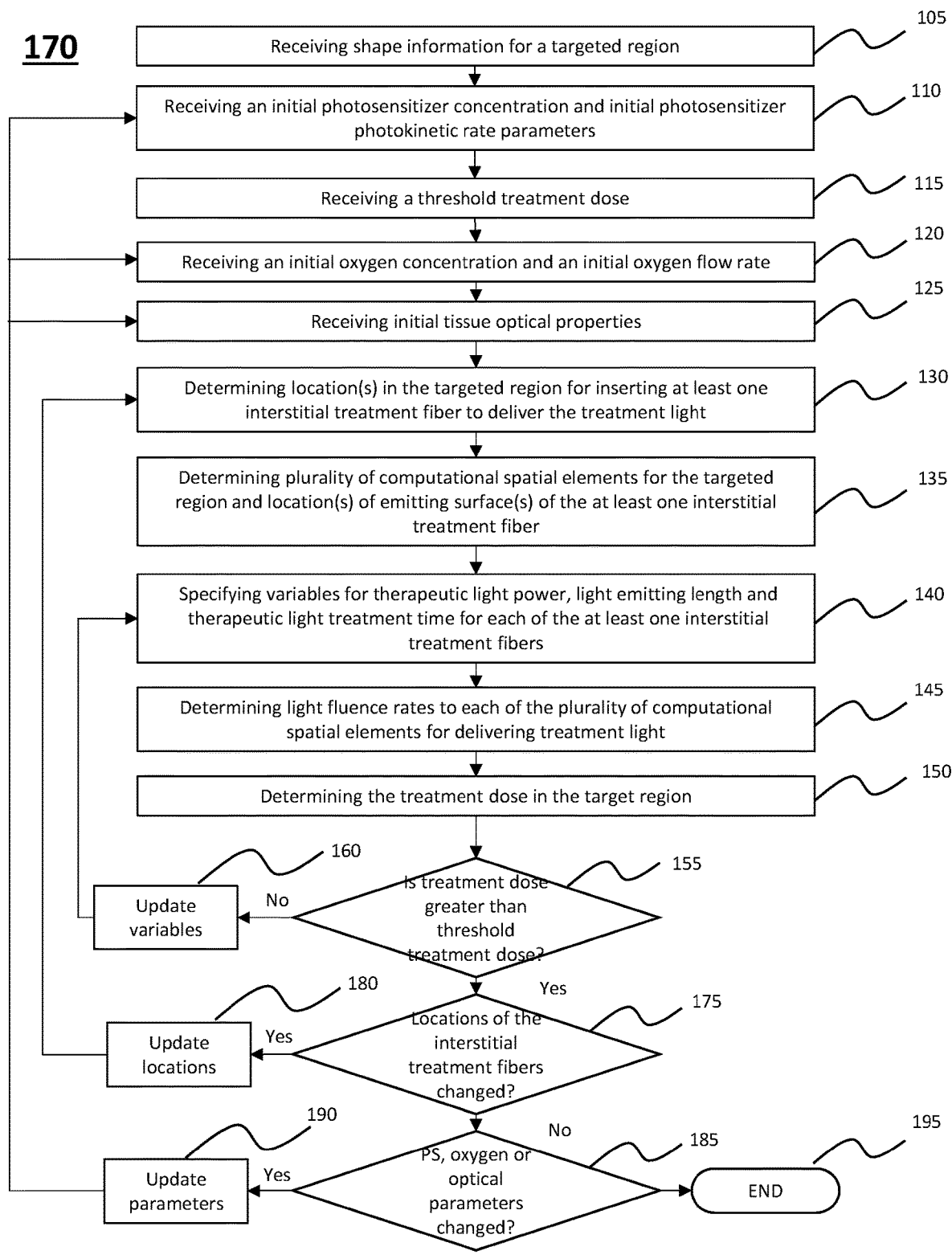
FIG. 3 schematically depicts another method for generating an interstitial photodynamic therapy plan.

FIG. 3 illustrates an alternative embodiment of the present disclosure. Method 170 illustrated in FIG. 3 includes the method illustrated in FIG. 2 and additional steps required for updating the locations of the interstitial fibers and/or for updating parameters including, but not limited to, the initial PS concentration, the initial PS photokinetic rate parameters, the initial oxygen concentration, the initial oxygen flow rate and the initial tissue optical parameters.

Method 170 includes 105, 110, 115, 120, 125, 130, 135, 140, 145 and 150 as in the method 100.

Further, as in the method 100, in method 170, at 155, it is determined whether the treatment dose greater than threshold treatment dose. Preferably the threshold treatment dose is a threshold PDT-dose or a threshold $[ROS]_{dose}$. The threshold $[ROS]_{dose}$ may be a threshold $[^1O_2]_{dose}$. It is more preferable that each treatment utilizing a primary threshold PDT-dose or primary threshold $[ROS]_{dose}$ optionally adds a secondary dose metric, where the secondary dose metric is a threshold fluence rate φ needed in order to kill cancer cells or where the secondary dose metric is a threshold light dose. Preferably method 170 determines that the treatment dose is greater than the threshold treatment dose for at least 80 percent of the computational spatial elements of the interior volume of the target region and optionally for at least 80 percent of the computational spatial elements of the boundary of the target region. More preferably method 170 determines that the treatment dose is greater than the threshold treatment dose for at least 90 percent of the computational spatial elements of the interior volume of the target region and optionally for at least 90 percent of the computational spatial elements of the boundary of the target region. Most preferably method 170 determines that the treatment dose is greater than the threshold treatment dose for all or substantially all of the computational spatial elements of the interior volume of the target region and optionally for all or substantially all of the computational spatial elements of the boundary of the target region.

If the answer is 'No', at 160 of method 170, the three variables (therapeutic light power, light emitting length and therapeutic light treatment time) for each at least one interstitial treatment fiber are updated. The method 170 then returns to 140 and repeats 140, 145, 150 and 155 until the treatment dose is greater than the threshold treatment dose in the preferred percent of the target region.

If the answer at 155 of the method 170 is 'Yes', the method 170 proceeds to 175, where it is determined whether the initial treatment plan location(s) of the interstitial treatment fibers have changed. If the answer is 'Yes', at, 180, the locations are updated. The method 170 then returns to 130 and repeats 130 to 175. If the answer is "No', method 170 proceeds to 185.

At 185 of the method 170 it is determined whether the initial treatment plan PS, oxygen or optical parameters have changed. If the answer is 'Yes', at 190, the parameters are updated. The new parameters are returned to 110, 120, 125, and 110 to 185 are repeated. If the answer is "No', the method 170 proceeds to 195, which terminates the simulation.

Other additional features may comprise methods that include a display means to enable a user to visualize a two-dimensional or a three-dimensional image of the treatment dose and/or a two-dimensional or a three-dimensional image of under- and over-doses and/or visualize fluence rates. In addition, the display means may also enable the user to visualize a two-dimensional or a three-dimensional image of the treatment dose and/or a two-dimensional or a three-dimensional image of under- and over-doses overlaid onto, respectively, a two-dimensional or a three-dimensional image of the shape information for the target region.

Furthermore, a method 100 or a method 170 of the present disclosure may include situations wherein the threshold treatment dose is a threshold light dose delivered at least at a threshold fluence rate.

In another aspect the present disclosure provides, systems for generating an interstitial photodynamic therapy treatment plans. Advantageously, the systems disclosed herein establish a treatment plan that will deliver at least a threshold treatment dose over the entire target region and that is also within an acceptable tolerance that will not significantly damage healthy tissue and organs-at-risk. The threshold treatment dose can be a threshold PDT-dose, a threshold $[ROS]_{dose}$ or a threshold light dose. Preferably the threshold treatment dose is a threshold PDT-dose or a threshold $[ROS]_{dose}$. The threshold $[ROS]_{dose}$ may be a threshold $[^1O_2]_{dose}$. It is more preferable that each treatment utilizing a primary threshold PDT-dose or primary threshold $[ROS]_{dose}$ optionally adds a secondary dose metric, where the secondary dose metric is a threshold fluence rate φ needed in order to kill cancer cells or where the secondary dose metric is a threshold light dose.

Figure 6:
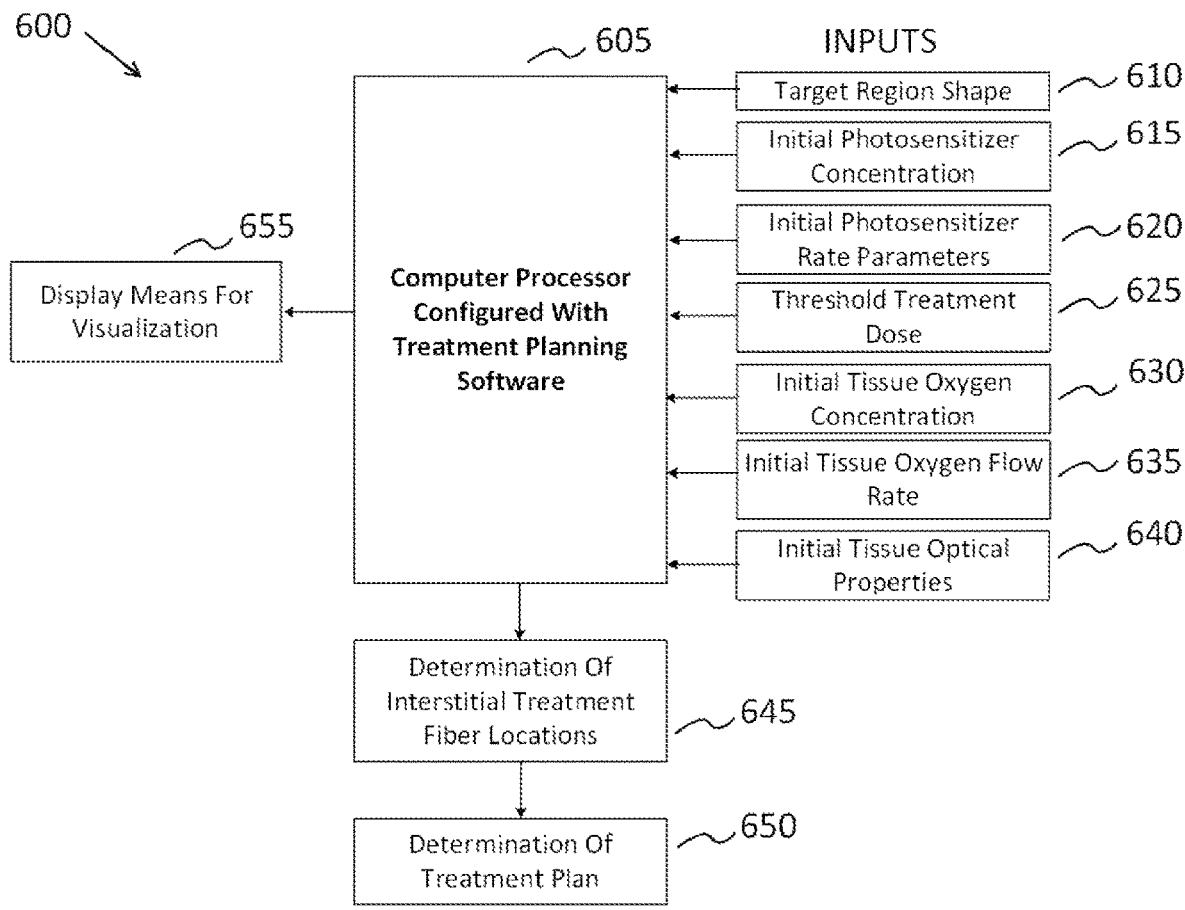
FIG. 6 is another schematic diagram of a system for generating an interstitial photodynamic therapy plan.

FIG. 6 schematically depicts a system for treatment planning 600 for optimizing light dose delivery to a target region in accordance with an embodiment of the present disclosure. The system comprises a computer processor 605 which is configured to receive input information for the treatment plan and to determine a treatment dose for a target region in a patient.

Figure 4:
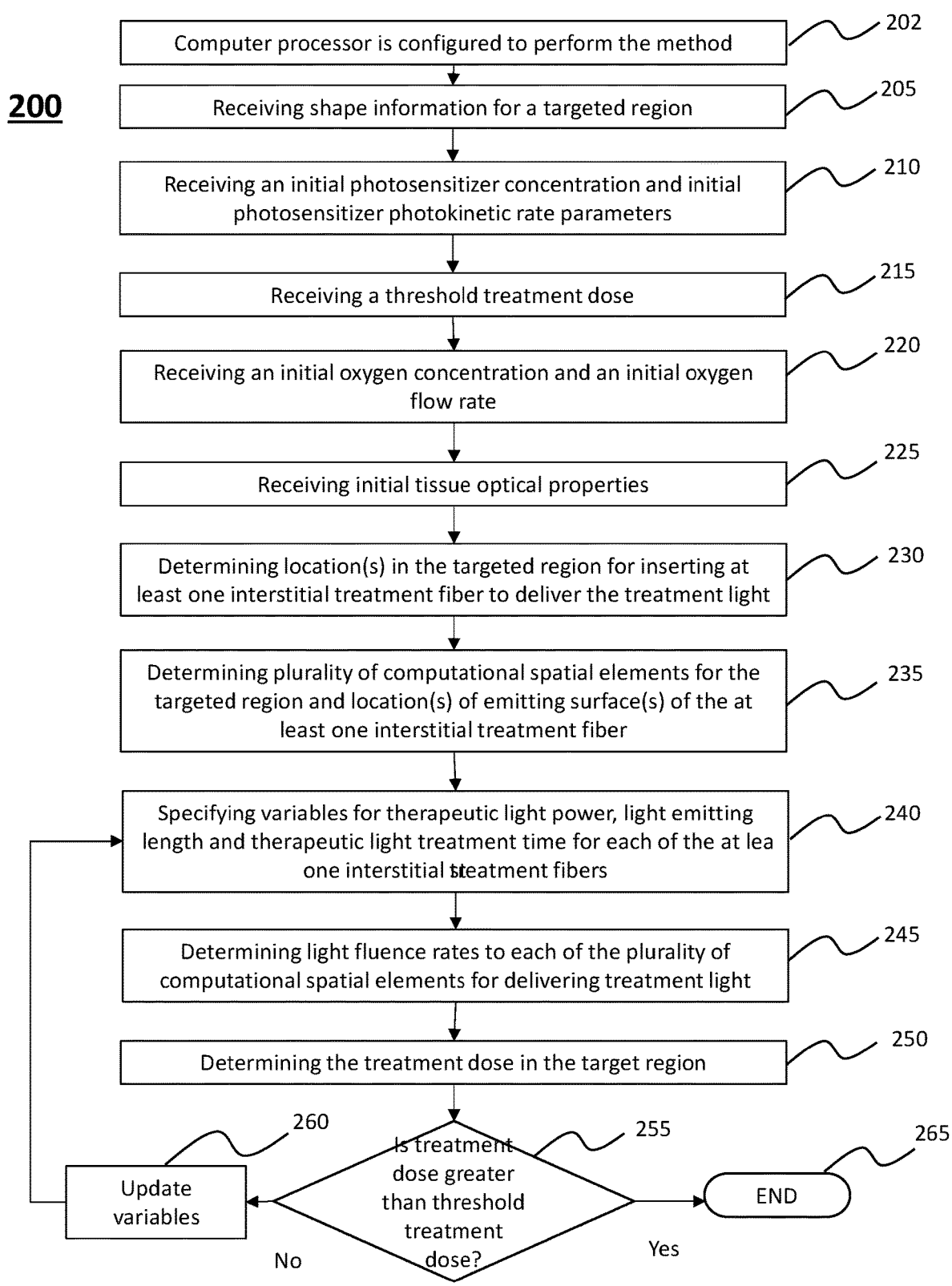
FIG. 4 schematically depicts a system for generating an interstitial photodynamic therapy plan.
Figure 5:
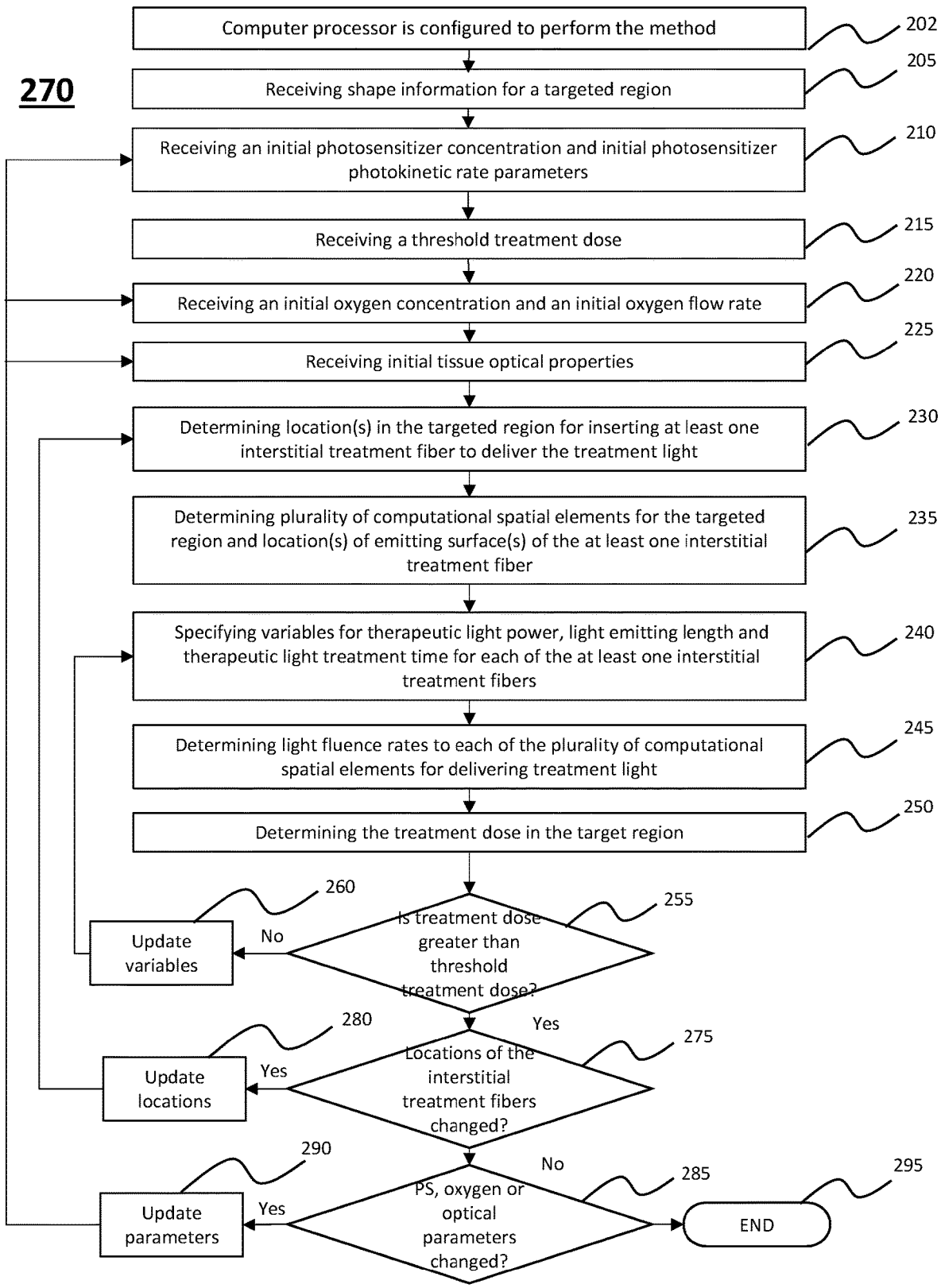
FIG. 5 schematically depicts another system for generating an interstitial photodynamic therapy plan.

In some embodiments, the system 600 includes a computer processor 605 configured to perform the method 100 illustrated in FIG. 2 or the method 170 illustrated in FIG. 3. For example, as depicted in FIG. 4, at 202, the computer processor 605 receives the information to perform the method 100. Similarly, FIG. 5 depicts the computer processor 605 performing the method 170 illustrated in FIG. 3. Computer processor 605 may comprise a multi-core processor and/or may comprise a plurality of computer processors. Computer processor 605 may further comprise one or more graphical processing units (GPUs) to reduce computing times.

The system 600 may further include inputs and outputs to the computer processor 605. The inputs to the computer processor 605 may include, but are not limited to, the target region shape 610, the initial photosensitizer concentration 615 in the target region, the initial photosensitizer rate parameters 620, the desired threshold treatment dose 625, the initial tissue oxygen concentration 630 in the target region, the initial tissue oxygen flow rate 635 into the target region and the initial tissue optical properties 640 in the target region. While not explicitly shown in FIG. 6, the system 600 may further include apparatus, such as various types of sensors, for obtaining the inputs 610, 615, 620, 625, 630, 635, and 640.

The outputs from the computer processor 605 include, but are not limited to, a determination of the interstitial treatment fiber locations 645, a determination of the treatment plan 650 and a display means 655 for visualization of, for example, the calculated treatment doses for all portions of the target region. The outputs 645 and 650 may be the result of performance of the method 100 or the method 170 by the computer processor 605.

While not explicitly shown, system 600 may further include apparatus for providing the treatment dose to the target region. The apparatus may include at least one power source, at least one light source, at least one interstitial treatment fiber, and at least one optical fiber to transmit light from the at least one light source to the at least one interstitial treatment fiber. The light source may include one or more light emitting diodes, one or more lasers, or a combination thereof. The wavelength of the light source is not particularly limited, but is dictated by the particular photosensitizer being used. Preferably, the at least one interstitial treatment fiber is a light diffusing interstitial treatment fiber.

As depicted in FIG. 4, the computer processor 605 performs the method 100 as follows. At step 202, the computer processor receives the information needed to perform the subsequent steps. For example, the computer processor may receive inputs depicted in FIG. 6 as 610, 615, 620, 625, 630, 635, and 640, in some embodiments. These received inputs are depicted in FIG. 4 as 205, 210, 215, 220 and 225.

The computer processor is configured to perform, at 205, wherein the computer processor receives information relating to the target region. The information relating to the target region may include, for example, the shape of the target region, the size of the target region, and/or the geometric coordinates of various portions of the target region. The information relating to the target region may be received from, for example, a computed tomography (CT) scan, a positron emission tomography (PET) scan, a magnetic resonance imaging (MRI) scan, an ultrasound image or a 3D camera image. CT scans and MRI scans, for example, provide in some embodiments, the raw data relating to the target region may be processed to obtain a 2-dimensional (2D) slice information about a 3-dimensional (3D) target region. The raw data may be processed using commercially-available or open-source geometry processing software packages. A 3D image of the target may then be constructed using the slice information, manually or automatically by outlining the target region in each slice, and using the outline to then construct a 3D image of the target region.

The computer processor may be further configured to perform, at 210, wherein the computer processor receives initial photosensitizer (PS) concentration and initial photosensitizer photokinetic rate parameters. The photosensitizer photokinetic rate parameters will be different for different photosensitizers. A table of photokinetic rate parameters for a variety of photosensitizers can be found in Kim et. al.; "On the in vivo photochemical rate parameters for PDT reactive oxygen species modeling," Phys. Med. Biol. 62 (2017) R1-R48.

The computer processor may be further configured to perform, at 215, wherein the computer processor receives threshold treatment dose information for the target region. Preferably the primary threshold treatment dose is a PDT-dose or a threshold $[ROS]_{dose}$. The threshold $[ROS]_{dose}$ may be a threshold $[^1O_2]_{dose}$. The threshold PDT-dose or the threshold $[ROS]_{dose}$ may be obtained from prior clinical data or from published or unpublished results. It is more preferable that each treatment utilizing a primary threshold PDT-dose or primary threshold $[ROS]_{dose}$ optionally add a secondary dose metric, where the secondary dose metric is a threshold fluence rate $\phi$ needed in order to kill cancer cells or where the secondary dose metric is a threshold light dose.

The threshold treatment dose can be delivered by all of the interstitial treatment fibers simultaneously to the entire target region or delivered sequentially in time by smaller sub-groups of the fibers to portions of the target region. Preferably an incremental treatment dose to a portion of the target region from a sub-group of one or more interstitial treatment fibers (that is part of the larger total number of interstitial treatment fibers) is included in the treatment dose only when the fluence rate to the portion of the target region from the sub-group is equal to or greater than a threshold fluence rate.

The computer processor may be further configured to perform, at 220, wherein the computer processor receives an initial oxygen concentration for the target region and an initial oxygen flow rate into the target region. The initial oxygen concentration and the initial oxygen flow rate can be determined by measurements taken on the target region of the patient. If measurement results are not available, data from published or unpublished results may be substituted.

The computer processor may be further configured to perform, at 225, wherein the computer processor receives receive initial tissue optical properties for the target region. Tissue optical properties can be determined by measurements taken on the target region of the patient. If measurement results are not available, data from published or unpublished results may be substituted. The tissue optical properties comprise the light absorption parameter, mua (or $\mu_a$), the light scattering parameter, mus (or $\mu_s$), the scattering anisotropy factor, $g_s$, and the index of refraction, n. Note that the scattering anisotropy factor, $g_s$, is a different parameter than the photokinetic parameter, g, for the oxygen intake rate. The tissue optical properties used in simulations of the threshold treatment dose may be different for each material (e.g. target region, healthy tissue, air).

The computer processor may be further configured to perform, at 230, wherein the computer processor determines, by manual input means or by actions of the processor, location(s) in the target region for inserting at least one interstitial treatment fiber to deliver the treatment light. Preferably the interstitial treatment fibers are surrounded by light-transmitting catheters. Light-transmitting catheters can be obtained commercially from vendors such as, for example, Best Medical International, Inc., Springfield, Va. The interstitial treatment fibers may be non-diffusing optical fibers or, preferably, each interstitial treatment fiber has a distal end that is a light diffusing interstitial optical fiber. Light diffusing interstitial optical fibers can be obtained from Medlight S.A., Switzerland. Standard diffuser lengths are 10, 15, 20, 25, 30, 40, 50, 70 mm. Manual means for determining locations of interstitial treatment fibers include letting the treating clinician decide on the positions of the interstitial treatment fibers. This may be required if there are treatment-sensitive organs-at-risk near the target region. In any case, the treating clinician makes the final decision on the positions of the interstitial treatment fibers. Another option for determining locations of interstitial treatment fibers is to use a standard brachytherapy transperineal implant template, which has a rectangular array of holes with 5 mm center-to-center separation that can be used to position light-transmitting catheters and interstitial treatment fibers in a regular or non-regular array. Once the positions of the one or more interstitial treatment fibers have been determined, one can use a geometry processing software package to create cylindrical holes into the computer-simulated 3D shape of the target region where the interstitial treatment fibers will be located.

The computer processor may be further configured to perform, at 235, wherein the computer processor determines a plurality of computational spatial elements for the target region and for the location(s) of the emitting surface(s) of at least one interstitial treatment fiber. Simulations of the treatment light dose can be done by Monte Carlo (MC) methods or Finite Element (FE) methods. Voxel elements or tetrahedral mesh elements can be used as the computational spatial elements for MC simulation. Tetrahedral mesh elements can be chosen as computational spatial elements for FE numerical calculations.

The computer processor may be further configured to perform, at 240, wherein the computer processor specifies initial values for the variables comprising therapeutic light power, light emitting length and therapeutic light treatment time for each at least one interstitial treatment fiber. This can be done by manual means or by automatic or semi-automatic optimization means.

The computer processor may be further configured to perform, at 245, wherein the computer processor determines the fluence rates to each of the plurality of computational spatial elements for delivering the treatment light. This step is preferably performed prior to using the photokinetic rate equations and the photosensitizer photokinetic rate parameters to calculate the treatment dose. The calculations can be performed using either MC or FE software, or any other suitable method.

The computer processor may be further configured to perform, at 250, wherein the computer processor determines the treatment dose to the interior volume and the boundary of the target region for each of the plurality of computational spatial elements. The determination of the treatment dose is performed using the fluence rates calculated at 245 for each of the plurality of computational spatial elements, as well as the photokinetic rate equations and the photosensitizer photokinetic rate parameters.

The computer processor may be further configured to perform, at 255, wherein the computer processor determines whether the treatment dose is greater than threshold treatment dose. The threshold treatment dose may be the threshold treatment dose received at 215. At 255, the computer processor further determines the portion of the interior volume of the target region that has received a treatment dose greater than the threshold treatment dose.

Preferably the threshold treatment dose is a threshold PDT-dose or a threshold $[ROS]_{dose}$. The threshold $[ROS]_{dose}$ may be a threshold $[^1O_2]_{dose}$. It is more preferable that each treatment utilizing a primary threshold PDT-dose or primary threshold $[ROS]_{dose}$ optionally adds a secondary dose metric, where the secondary dose metric is a threshold fluence rate $\phi$ needed in order to kill cancer cells or where the secondary dose metric is a threshold light dose. For effective treatment, it is preferred that the treatment dose is greater than the threshold treatment dose for at least 80 percent of the computational spatial elements of the interior volume of the target region and optionally for at least 80 percent of the computational spatial elements of the boundary of the target region. More preferably the treatment dose is greater than the threshold treatment dose for at least 90 percent of the computational spatial elements of the interior volume of the target region and optionally for at least 90 percent of the computational spatial elements of the boundary of the target region. Most preferably the treatment dose is greater than the threshold treatment dose for all or substantially all of the computational spatial elements of the interior volume of the target region and optionally for all or substantially all of the computational spatial elements of the boundary of the target region.

The computer processor may be further configured to perform, at 260, wherein the computer processor, in response to a determination that at least a predetermined portion of the target region did not receive a treatment dose greater than the threshold treatment dose, updates one or more of variables including therapeutic light power, light emitting length and therapeutic light treatment time for each at least one interstitial treatment fiber, returns to 240, and repeats corresponding of 240, 245, 250 and 255 until the treatment dose for at least the predetermined portion of the target region is greater than the threshold treatment dose. Note that increasing the therapeutic light power increases the fluence rate.

On the other hand, the computer processor of the system 200 may be configured to perform a step 265, wherein the computer processor, in response to a determination that at least a predetermined portion of the target region received a treatment dose greater than the threshold treatment dose, terminates the simulation.

At 240, 245, 250, 255, 260 and 265, where needed, optimization of corresponding parameters can be performed using software programs such, for example, one disclosed in U.S. Pat. No. 8,986,358 or convex optimization disclosed in Yassine et al., "Automatic interstitial photodynamic therapy planning via convex optimization," Biomedical Optics Express, Vol. 9, No. 2 (1 Feb. 2018). Optionally for a system of this invention, the computer processor is configured to calculate a treatment dose wherein the treatment dose is a light dose delivered at least at a threshold fluence rate.

In an example of a system that can be utilized for generating an interstitial photodynamic therapy treatment plan, the system may calculate, for example, the fluence rate, PDT-dose, $[ROS]_{dose}$, $[^1O_2]_{dose}$ and light dose for each of the plurality of computational spatial elements for interstitial photodynamic therapy. The system may combine, in one integrated device, FE or MC simulations of light transport, fluence rate and light dose (fluence) as well as photokinetics (PK) simulations of $[ROS]_{dose}$, $[^1O_2]_{dose}$, and PDT-dose. The system may perform fluence rate simulations for each of the plurality of computational spatial elements using the light power of the interstitial treatment fibers and the tissue optical properties of the target region as inputs. The PK simulations may use the fluence rate results plus inputs of PS concentration, PS photokinetics parameters, tissue oxygen concentration and oxygen flow rates to calculate $[ROS]_{dose}$, $[^1O_2]_{dose}$, and PDT-dose. The calculated PDT photokinetics may include light-PS-excitation, the PS-to-oxygen excitation to generate singlet oxygen, the singlet oxygen reaction with the target region and the singlet oxygen reaction with the PS (resulting in photobleaching). In some embodiments, graphics on the system may display 2D and 3D outputs of light fluence (light dose), fluence rate, PDT-dose, $[ROS]_{dose}$ and $[^1O_2]_{dose}$ at every computational spatial element in the 3D target. A clinician can use this information to localize areas of under-treatment and make corrections to the treatment plan.

In some embodiments, the computer processor 605 of the system 600 can be further configured to perform additional steps as illustrated in FIG. 5. The steps illustrated in FIG. 4 are performed after the shape of the target region has been obtained using, for example, a computed tomography (CT) scan, a positron emission tomography (PET) scan, a magnetic resonance imaging (MRI) scan, an ultrasound image or a 3D camera image, but before a clinician begins treatment.

Once the clinician inserts interstitial treatment fibers into the target region, however, the clinician may find that the locations of the interstitial treatment fibers are different than in the initial treatment plan. The initial interstitial photodynamic therapy treatment plan parameters should be updated to take into account the change(s) in the location(s) of the at least one interstitial treatment fiber for the target region that have occurred since the interstitial photodynamic therapy treatment plan was first generated. In addition, the interstitial photodynamic therapy treatment plan may need to be updated before or during the treatment if there are measurements showing changes in parameters for the target region in at least one of the initial photosensitizer concentration, the plurality of initial photosensitizer photokinetic rate parameters, the initial tissue oxygen concentration, the initial tissue optical properties or the initial oxygen flow rate.

As depicted in FIG. 5, the computer processor 605 performs the method 170 depicted in FIG. 3 by performing the operations as depicted in FIG. 4 and the additional operations, illustrated in FIG. 5, for updating the locations of the interstitial fibers and/or for updating parameters including, but not limited to, the initial PS concentration, the initial PS photokinetic rate parameters, the initial oxygen concentration, the initial oxygen flow rate and the initial tissue optical parameters.

Operations at 202 to 250 in in FIG. 5 are identical to those at 202 to 250 in FIG. 4. However, when performing the method 170, as shown in FIG. 5, the computer processor may be configured to perform 255, wherein the computer processor determines whether the treatment dose is greater than threshold treatment dose, that is received at 215. Preferably the threshold treatment dose is a threshold PDT-dose or a threshold $[ROS]_{dose}$. The threshold $[ROS]_{dose}$ may be a threshold $[^1O_2]_{dose}$. It is more preferable that each treatment utilizing a primary threshold PDT-dose or primary threshold $[ROS]_{dose}$ optionally adds a secondary dose metric, where the secondary dose metric is a threshold fluence rate $\phi$ needed in order to kill cancer cells or where the secondary dose metric is a threshold light dose. The computer processor of system 270, at 255, further determines the portion of the interior volume of the target region that has received a treatment dose greater than the threshold treatment dose.

For effective treatment, it is preferred that the treatment dose is greater than the threshold treatment dose for at least 80 percent of the computational spatial elements of the interior volume of the target region and optionally for at least 80 percent of the computational spatial elements of the boundary of the target region. More preferably the treatment dose is greater than the threshold treatment dose for at least 90 percent of the computational spatial elements of the interior volume of the target region and optionally for at least 90 percent of the computational spatial elements of the boundary of the target region. Most preferably the treatment dose is greater than the threshold treatment dose for all or substantially all of the computational spatial elements of the interior volume of the target region and optionally for all or substantially all of the computational spatial elements of the boundary of the target region.

Referring back to FIG. 5, the computer processor may be further configured to perform 260, wherein the computer processor, in response to a determination that at least a predetermined portion of the target region did not receive a treatment dose greater than the threshold treatment dose, updates one or more of variables including therapeutic light power, light emitting length and therapeutic light treatment time for each at least one interstitial treatment fiber, returns to 240, and repeats corresponding of 240, 245, 250 and 255 until the treatment dose for at least the predetermined portion of the target region is greater than the threshold treatment dose. Note that increasing the therapeutic light power increases the fluence rate.

On the other hand, if it is determined that at least a predetermined portion of the target region has received a treatment dose greater than the threshold treatment dose, at 275, the computer processor may determine whether initial treatment plan location(s) of the interstitial treatment fibers has changed. The computer processor, in response to a determination that initial treatment plan location(s) of the interstitial treatment fibers has changed, at 280, may update the location(s) of the interstitial treatment fibers by manual means or by actions of the processor, then returns to 230 and repeats 230 to 275. Manual means for determining locations of interstitial treatment fibers include letting the treating clinician decide on the positions of the interstitial treatment fibers. In any case, the treating clinician makes the final decision on the positions of the interstitial treatment fibers. However, if it is determined that the initial treatment plan location(s) of interstitial treatment has not changed, the computer processor proceeds to 285.

The computer processor may be further configured to determine, at 285, whether any of initial treatment plan PS, oxygen or optical parameters have changed. In response to a determination that at least one of PS, oxygen or optical parameters have changed, at 290, the computer processor updates the changed parameters, returns the new parameters to corresponding of the 210, 220, 225, and repeats 210 to 285. On the other hand, if the initial treatment plan parameters are determined not to have changed, the computer processor proceeds to 295, which ends the simulation.

In some embodiments, the system 600 for generating an interstitial photodynamic therapy treatment plan may further include one or more additional components. For example, in some embodiments, the system 600 may include at least one therapeutic treatment light source such as, for example, a laser or light-emitting diode.

In some embodiments, the system may include at least one interstitial treatment fiber functionally coupled to the at least one therapeutic treatment light source for delivering deliver the treatment light to the target region. In such embodiments, a distal end of least one interstitial treatment fiber is preferably a light diffusing interstitial treatment fiber.

In some embodiments, the system includes a diagnostic light source functionally coupled to an interstitial diagnostic fiber. In some embodiments, the diagnostic light source may be the same as the treatment light source. In such embodiments, the system additionally includes optics for bifurcating the light from the treatment light source into a second light source that functions as the diagnostic light source. In some embodiments, the diagnostic light source is separate from the treatment light source. In such embodiments, the diagnostic light source and the treatment light source may or may not be powered using a same power source.

In some embodiments, the system includes at least one interstitial detector to detect diagnostic light generated by the diagnostic light source and/or treatment light generated by the therapeutic treatment light source and/or photosensitizer fluorescence generated by the diagnostic light source or the treatment light source. The detector may include, for example, one or more photodiodes.

In some embodiments, the system includes at least one spectrophotometer functionally coupled to the at least one interstitial detector to detect the treatment light intensity and/or the diagnostic light intensity and/or the fluorescence light intensity generated by the therapeutic treatment light source or the diagnostic light source.

In some embodiments, the system includes one or more light-transmitting catheters enclosing the at least one therapeutic interstitial treatment fiber, the at least one interstitial diagnostic fiber and the at least one interstitial detector.

In some embodiments, the system includes a display to enable a user to visualize a two-dimensional or three-dimensional image of the treatment dose and/or a two-dimensional or three-dimensional image of under- and over-doses and/or visualize fluence rates. In addition, the display means may also enable the user to visualize a two-dimensional or three-dimensional image of the treatment dose and/or a two-dimensional or three-dimensional image of under- and over-doses overlaid onto, respectively, a two-dimensional and/or three-dimensional image of the shape information for the target region.

Figure 7:
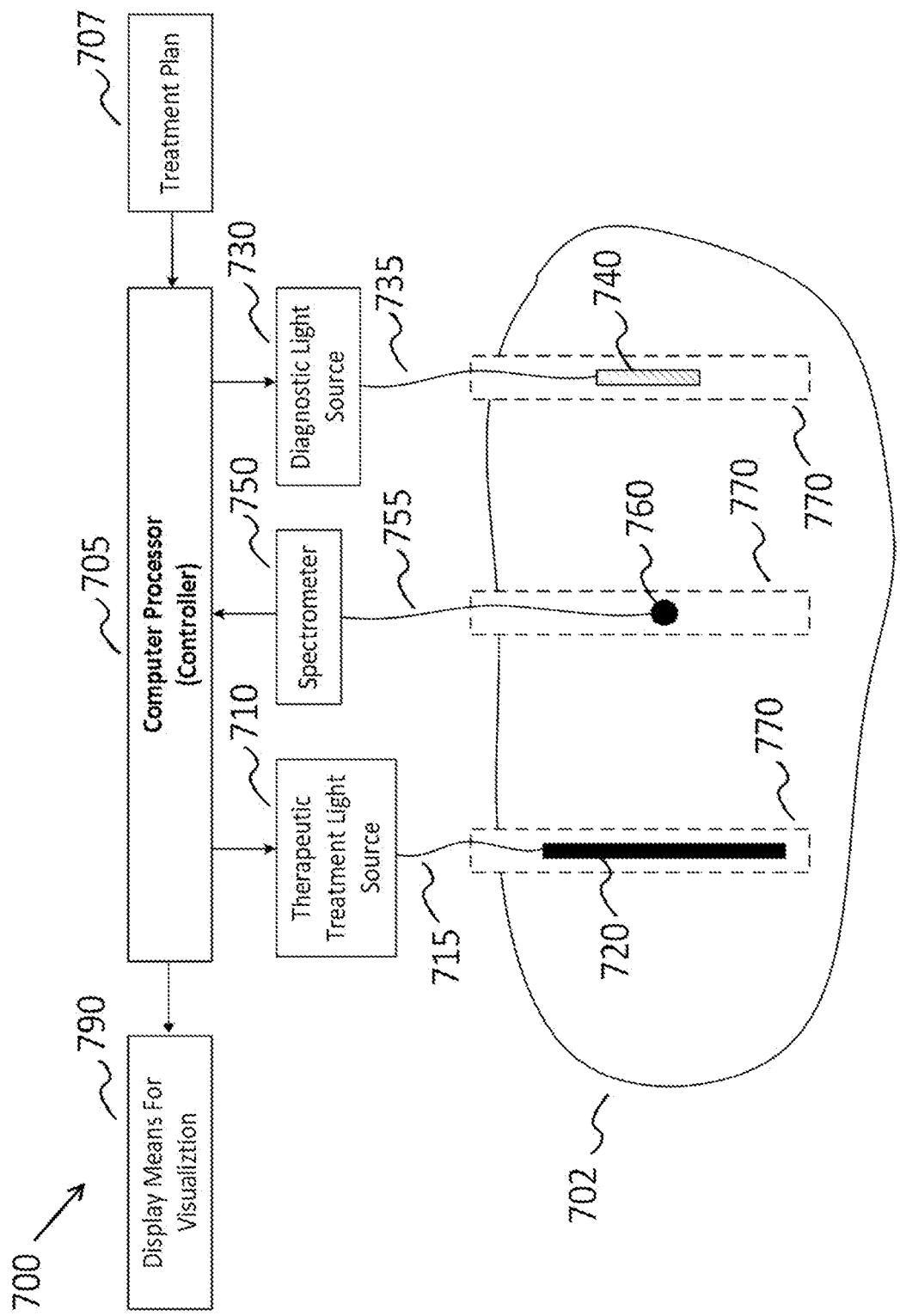
FIG. 7 is a schematic diagram of a system for delivering interstitial photodynamic therapy along with a cross-sectional view of a target region.

FIG. 7 illustrates another example of a system 700 for treatment planning that includes the means for delivering and monitoring the treatment plan in a target region. For illustrative purposes, system 700 in FIG. 7 is greatly simplified to include only one light diffusing interstitial optical fiber 720 for providing treatment light to the target region 702, one interstitial detector 760 for diagnostic monitoring and, optionally, one light diffusing interstitial optical fiber 740 for delivering diagnostic light for diagnostic monitoring. In contrast to this simplified system, a typical treatment planning system used in the clinic that includes means for delivering and monitoring the treatment plan may have a plurality of light diffusing interstitial optical fibers 720 for delivering treatment light to the target region 702, a plurality of interstitial detectors 760 for diagnostic monitoring, and, optionally, a plurality of light diffusing interstitial optical fibers for delivering diagnostic light for diagnostic monitoring.

System 700 in FIG. 7 comprises a computer processor 705, which acts as a controller for system 700. Computer processor 705 may optionally be substantially the same computer processor as utilized in system 600. The computer processor 705 may optionally be configured to perform the method 100 or the method 170. In some embodiments, computer processor 705 can control the therapeutic treatment light source 710 and diagnostic light source 730 as well as receive information from spectrometer 750.

Therapeutic treatment light source 710 may be any light source that emits light of the proper wavelength (or wavelength range) to be absorbed by the PS that has previously been injected or otherwise transported to target region 702. Example therapeutic treatment light sources 710 include, but are not limited to, continuous wave (CW) lasers, pulsed lasers, fiber optic lasers, light emitting diodes (LEDs), fluorescent light sources (wavelength filtered or unfiltered), or incandescent light sources (wavelength filtered or unfiltered). Preferred therapeutic treatment light sources 710 are CW lasers, fiber optic lasers and LEDs.

Light from the therapeutic treatment light source 710 is preferably transmitted to the target region 702 by an interstitial treatment fiber 715. Preferably the distal end of the interstitial treatment fiber 715 is a light-diffusing interstitial treatment fiber 720. Light-diffusing interstitial optical fibers can be obtained from, for example, Medlight S.A., Switzerland. Standard diffuser lengths are 10, 15, 20, 25, 30, 40, 50, 70 mm. However, other lengths are contemplated within the scope of the present disclosure.

Diagnostic light source 730 may be any light source that emits light of the proper wavelength to monitor the I-PDT. The monitoring light could have the same wavelength (or wavelength range) as the therapeutic treatment light source or the wavelength could be different. One can monitor the I-PDT at the same wavelength as the therapeutic light source, but at a lower intensity, to monitor any changes in the optical properties of the target region. Changes in the optical properties can occur, for example, when oxygen is depleted from the target region as a result of the I-PDT. An example of a wavelength that is different from the therapeutic treatment light is any wavelength that can excite fluorescence of the PS. Monitoring the fluorescence emission of the PS allows for monitoring changes in the concentration of the PS due to photobleaching resulting from the I-PDT. Without wishing to be bound by theory, changes in the PS concentration may affect the resulting PDT-dose or the resulting reactive oxygen species dose. Example diagnostic light sources 730 include, but are not limited to, continuous wave (CW) lasers, pulsed lasers, fiber optic lasers, light emitting diodes (LEDs), fluorescent light sources (wavelength filtered or unfiltered), or incandescent light sources (wavelength filtered or unfiltered). Preferred diagnostic light sources 730 are CW lasers, fiber optic lasers and LEDs.

Light from the diagnostic light source 730 is preferably transmitted to the target region 702 by an interstitial diagnostic fiber 735. Preferably the distal end of the interstitial diagnostic fiber 735 is a light-diffusing interstitial diagnostic fiber 740.

The I-PDT process can be monitored using an interstitial detector 760 functionally coupled to spectrometer 750 via an interstitial optical fiber 755. The interstitial detector 760 can measure the intensity of treatment light coming from the light-diffusing interstitial treatment fiber 720 or the intensity of diagnostic light coming from the light-diffusing interstitial diagnostic fiber 740 or fluorescence emission from the PS that is excited by the light-diffusing interstitial diagnostic fiber 740 or excited by the light-diffusing interstitial treatment fiber 720. Interstitial detectors are available from, for example, Medlight S.A., Switzerland.

Light-diffusing interstitial optical fiber 720, interstitial detector 760 and light-diffusing interstitial diagnostic fiber 740 are preferably enclosed in hollow, light-transmitting catheters 770. Light-transmitting catheters 770 can be obtained from, for example, Best Medical International, Inc., Springfield, Va.

System 700 optionally includes a display 790 for visualizing the treatment plan and for monitoring the progress of the treatment. For example, the display can enable a user to visualize a two-dimensional or three-dimensional image of the treatment dose and/or a two-dimensional or three-dimensional image of under- and over-doses and/or visualize fluence rates. In addition, the display means may also enable the user to visualize a two-dimensional or a three-dimensional image of under- and over-doses overlaid onto, respectively, a two-dimensional or three-dimensional image of the shape information for the target region.

In some embodiments, the system 700, or parts thereof can be executed using a mobile device such as, for example, a mobile phone or a tablet computer. For example, the computer processor 705 and the display 790 may be those of a mobile phone or a tablet computer, while a data bus can connect the treatment light source, the diagnostic light source and the spectrometer to the mobile phone or the tablet computer.

EXAMPLES

Figure 8:
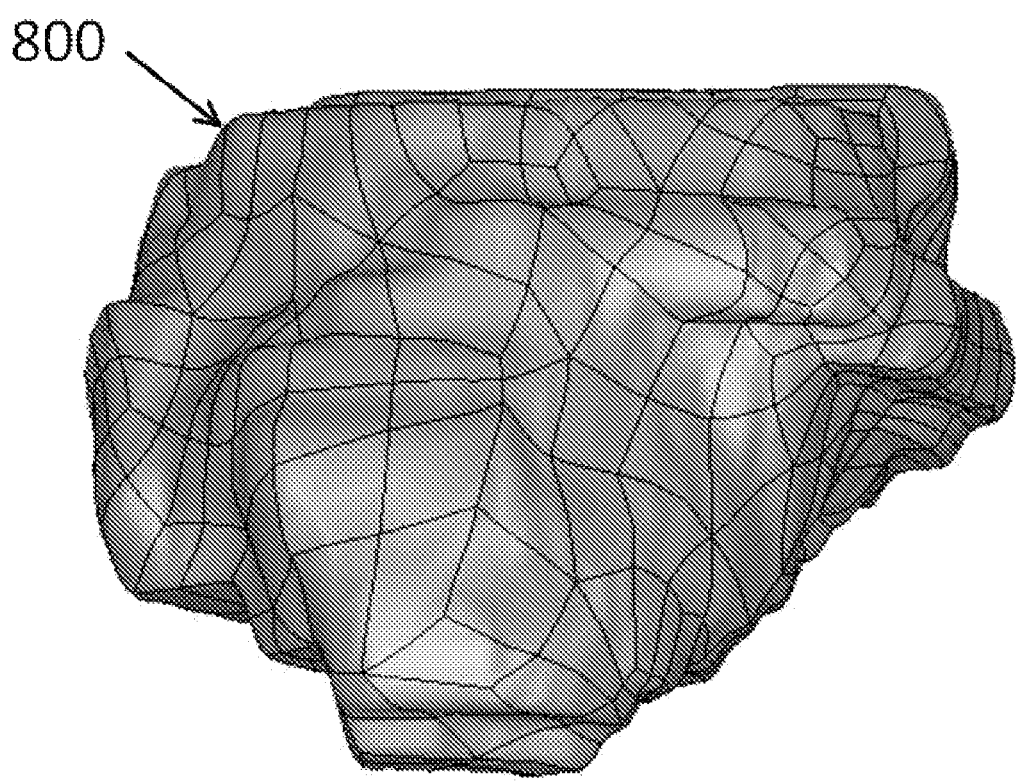
FIG. 8 is a view of a target region.

Example 1: Generating a Tetrahedral Mesh for the Target Region and One Interstitial Light Source The shape 800 of an example target region is shown in FIG. 8. Slice information for the target region was obtained using magnetic resonance imaging (MRI) scans. A 3D image processing software was used to process the slice information, construct a 3D shape, and output the shape as a set of NURBS surfaces. FIG. 8 shows the resulting shape 800 as viewed in a geometry processing software viewer.

Figure 9:
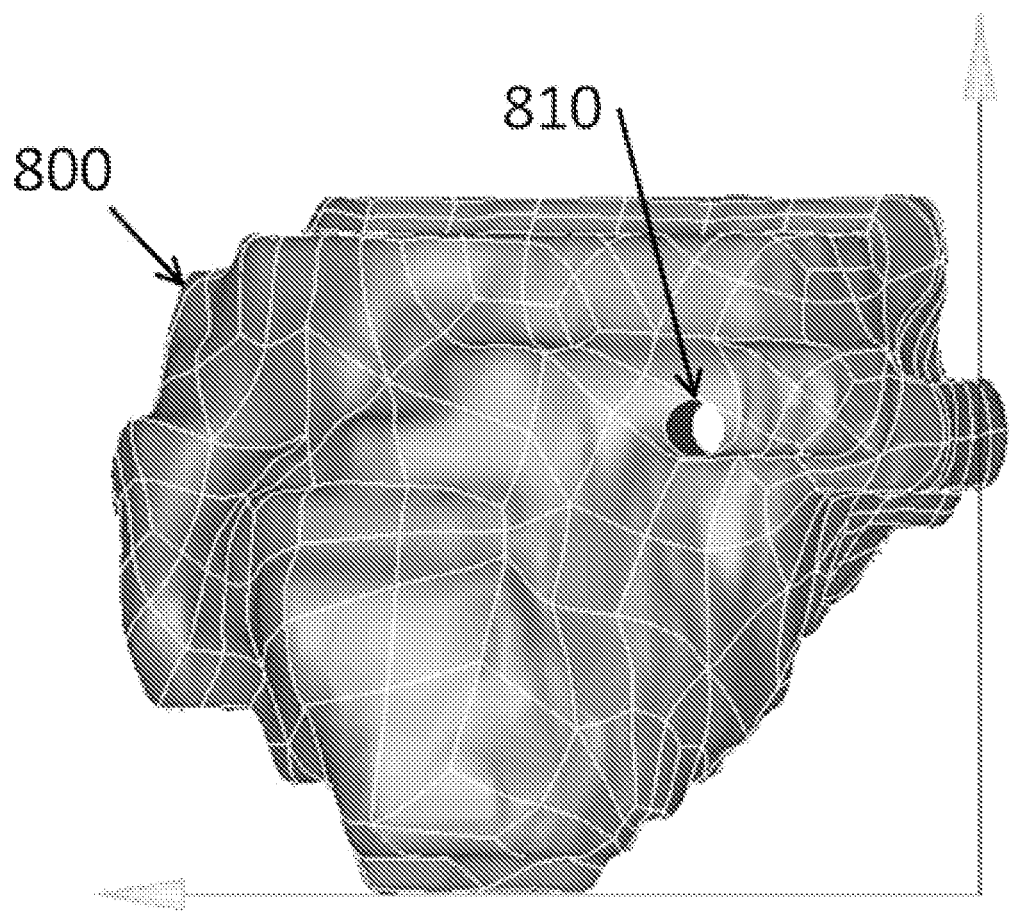
FIG. 9 is a view of a target region with a hole.

In general, the locations of one or more interstitial treatment fibers are determined by manual or automatic means. For illustrative purposes in this example, FIG. 9 shows the location of one interstitial treatment fiber in target region 800. An open-source or a commercially available geometry processing software can be used to create the cylindrical hole 810 into the computer-generated 3D shape of the target region 800 where the interstitial treatment fiber will be located.

Figure 10:
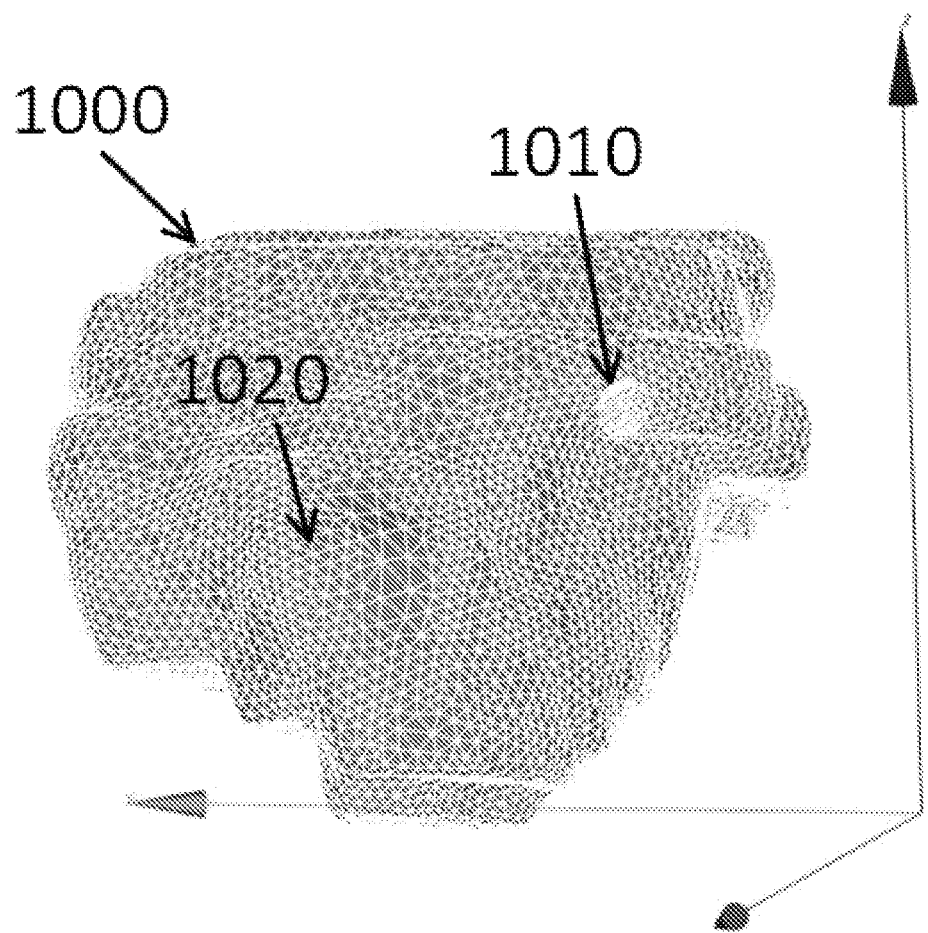
FIG. 10 is a view of a target region with a hole showing surface faces and nodes of a tetrahedral mesh.
Figure 11:
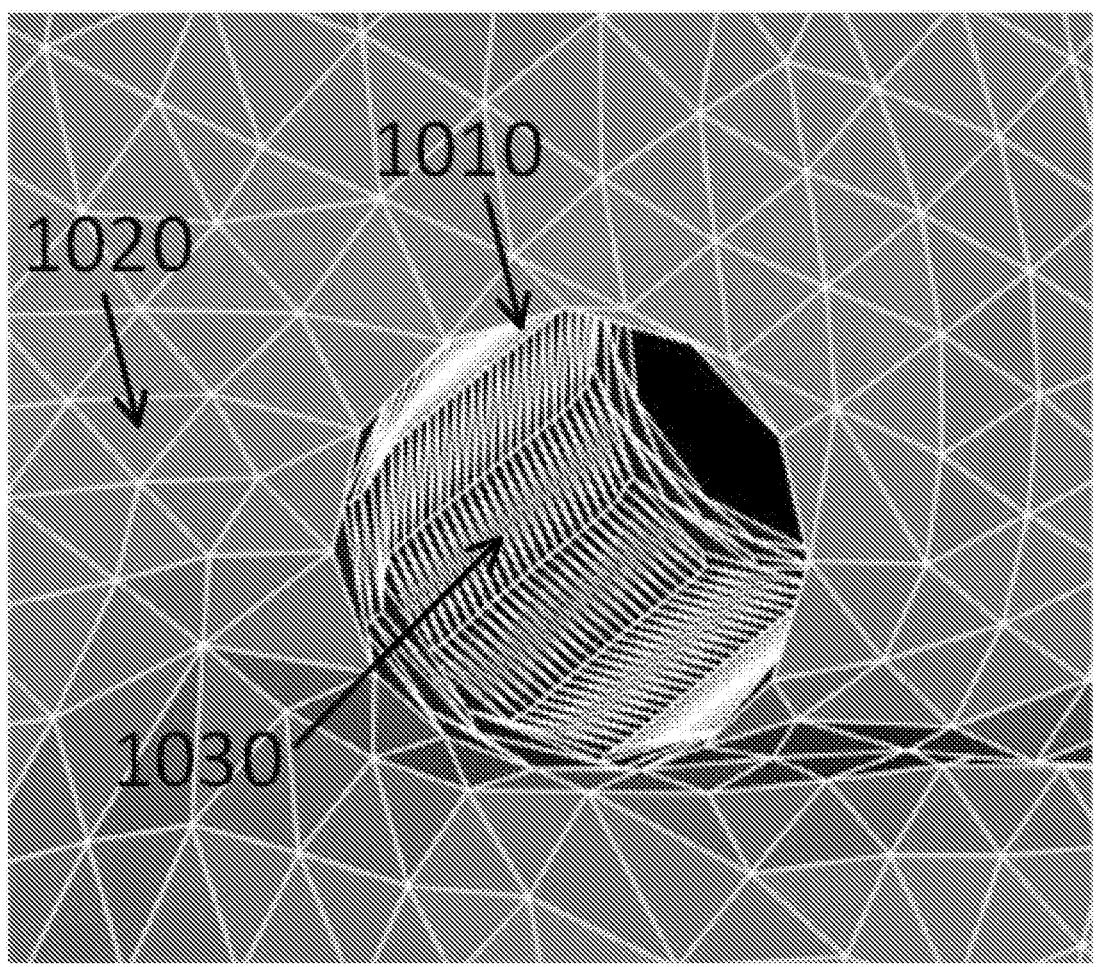
FIG. 11 is a partial view of a target region with a hole showing surface faces and nodes of a tetrahedral mesh, including surface faces and nodes of tetrahedral mesh in the hole.

A plurality of computational spatial elements for the target region and for the location of the emitting surface for the one interstitial treatment fiber were then determined. Computational spatial elements for FE methods were used, which are tetrahedral mesh elements. An initial tetrahedral mesh can be generated by an open-source or commercially available geometry processing software packages. This initial FE mesh has unlabeled mesh faces and nodes. FIG. 10 shows the target region 1000, the cylindrical hole 1010 and the tetrahedral mesh 1020. For simplicity, only the surface triangular faces and nodes are shown (the nodes are located at the corner of the triangles). The surface of the cylindrical hole 1010 also is covered by the tetrahedral mesh 1030 as shown in an expanded view in FIG. 11. The surface mesh 1030 defines the emitting surface for the interstitial treatment fiber. Later the mesh faces and nodes are labeled in order to do FE simulations.

Example 2: Determining Fluence Rates for the Target Region

Figure 12:
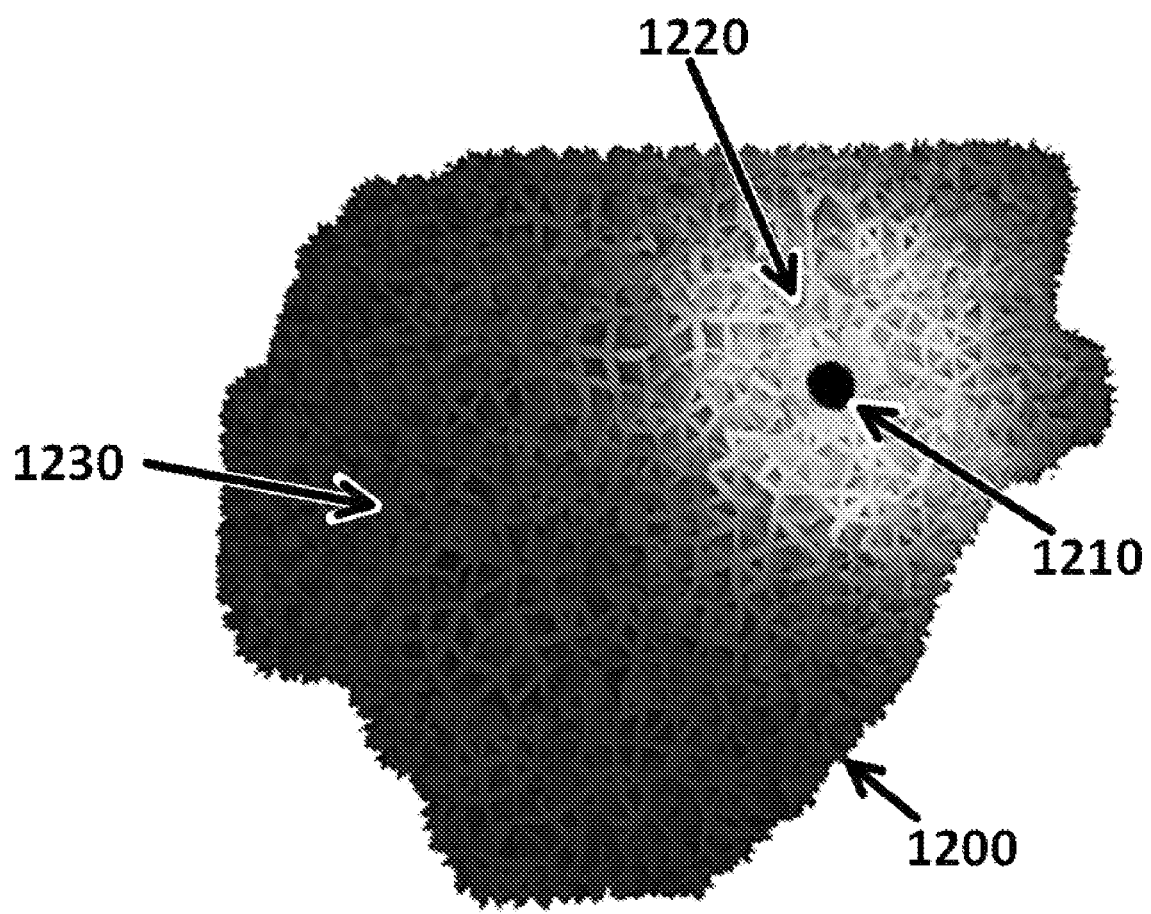
FIG. 12 shows a portion of a target region that receives a threshold fluence rate.
Figure 13:
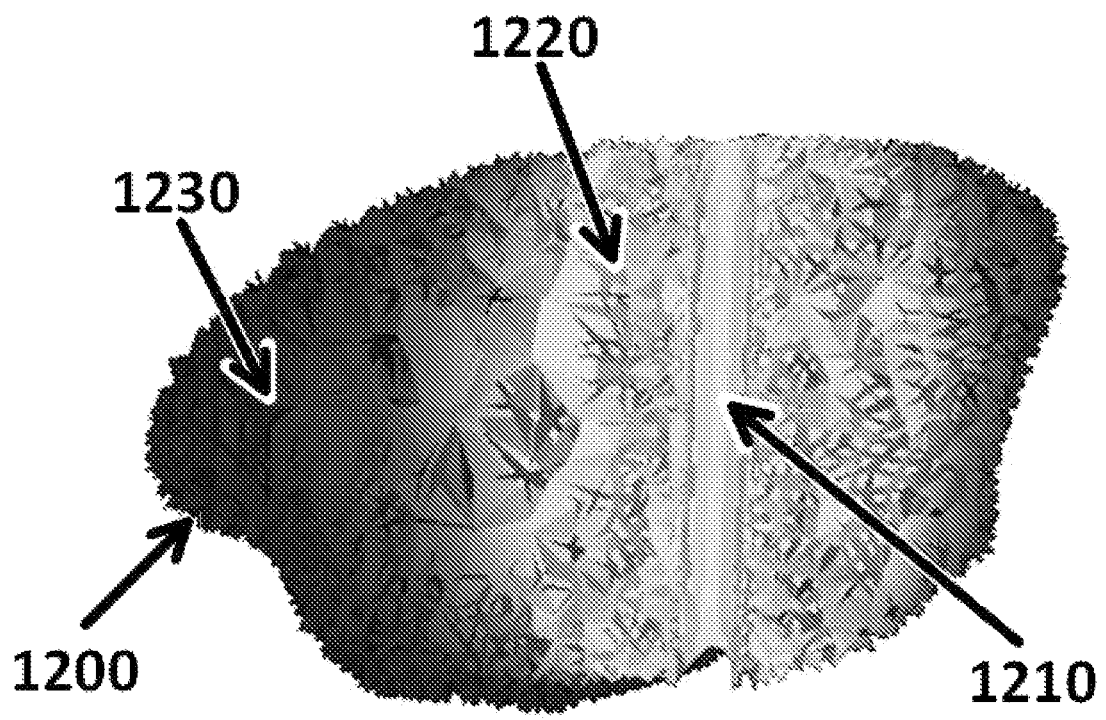
FIG. 13 shows a cross sectional view of a portion of a target region and a portion of the surface of the hole that receive a threshold fluence rate.

The shape 1200 of an example target region is shown in FIG. 12. Hole 1210 is the location for an interstitial treatment fiber. In this case the interstitial treatment fiber is a light-diffusing interstitial fiber that has an emitting power of 200 mW/cm. Dosie™, a proprietary software, was used to estimate by the FE method the fluence rates for the plurality of computational spatial elements, where the computational spatial elements are tetrahedral mesh elements. The tissue optical parameters for the target region are the light absorption parameter mua=0.05 $mm^{-1}$, the light scattering parameter mus=3.8 $mm^{-1}$, the scattering anisotropy factor, $g_s$=0.9, and the index of refraction, n=1.37. The results are shown in FIG. 12 and FIG. 13. FIG. 12 shows the fluence rate values rendered over the outside surface of the target volume. FIG. 13 is a cross sectional view revealing the fluence rate values over the inside surface of the hole 1210. The graphical outputs are set to show the regions of the target area that receive a threshold fluence rate of 8.4 $mW/cm^2$ (the threshold fluence rate shown in TABLE 4 for mice). In the 'lighter' regions 1220, the fluence rate is equal to or greater than 8.4 $mW/cm^2$. In the 'darker' regions 1230 of the target, the fluence rate is less than 8.4 $mW/cm^2$, indicating that inserting at least another light source fiber may be required to ensure that all the spatial elements receive the threshold fluence rate.

Example 3: Determine PDT-Dose for the Target Region

Figure 14:
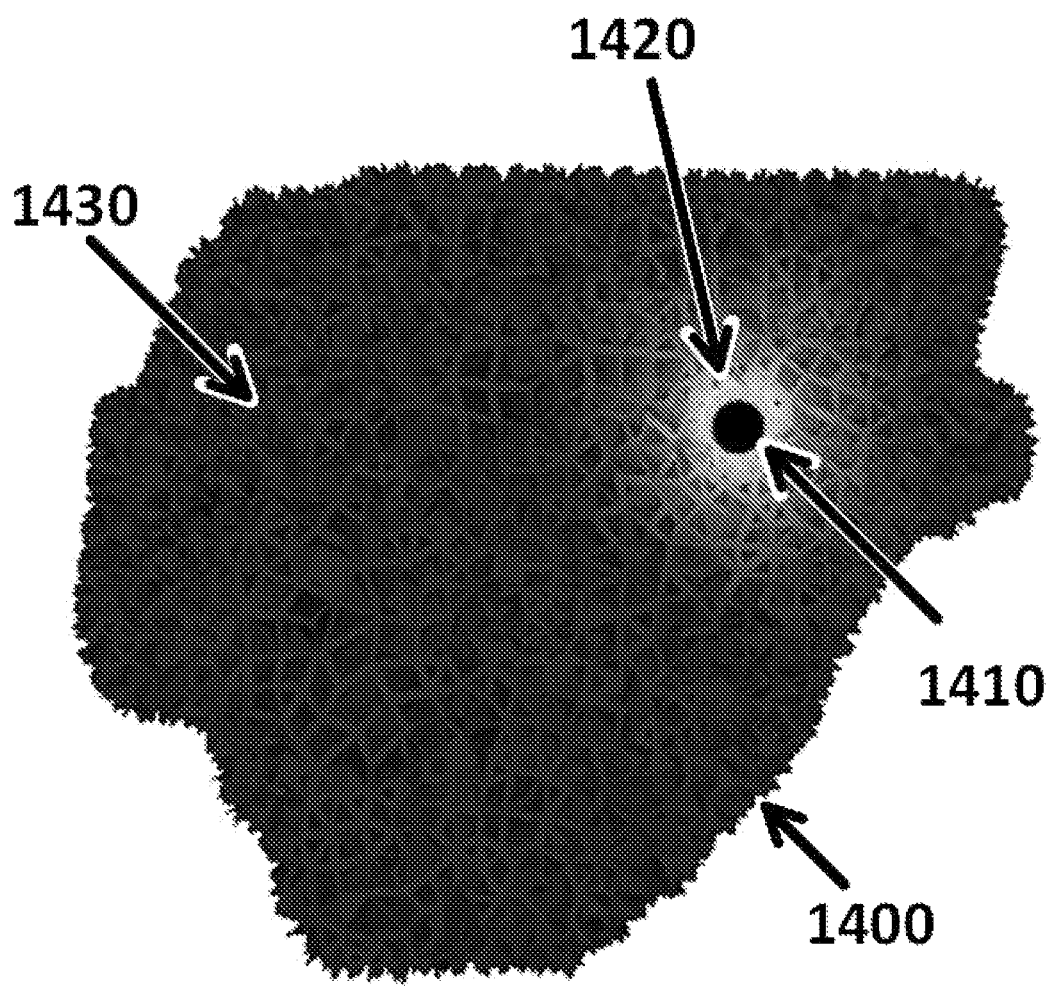
FIG. 14 shows a portion of a target region that receives a threshold PDT-dose.
Figure 15:
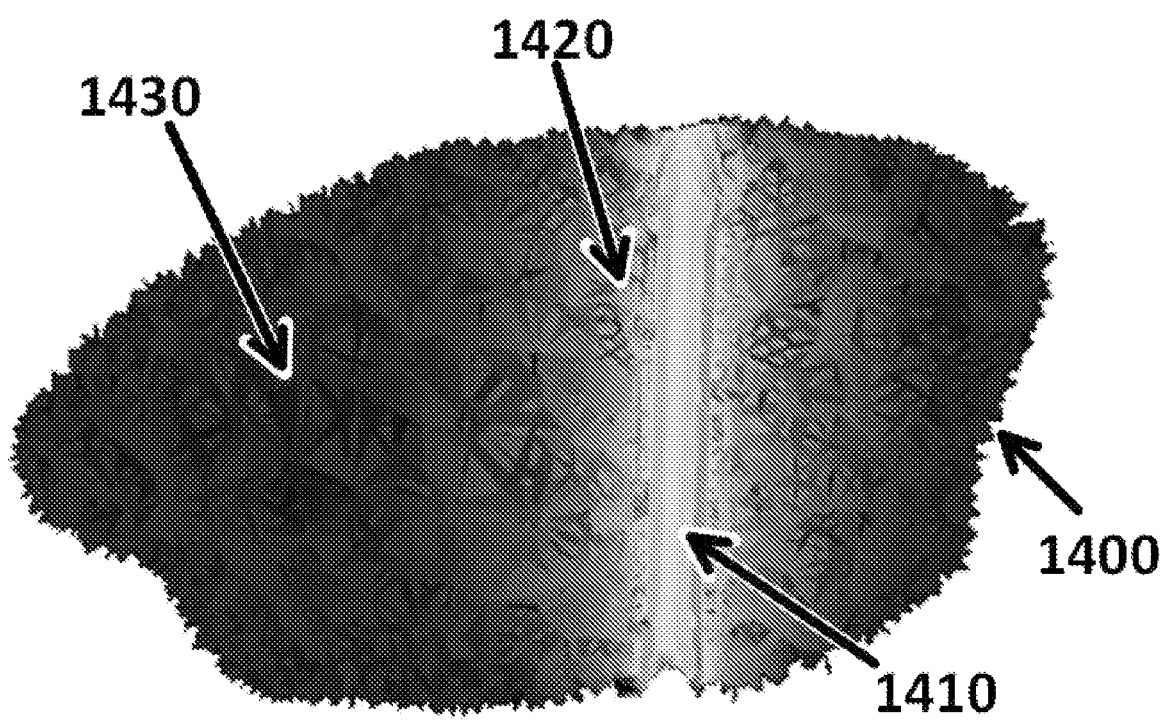
FIG. 15 shows a cross sectional view of a portion of a target region and a portion of the surface of the hole that receive a threshold PDT-dose.

Using the calculated fluence rates for the tetrahedral mesh elements from Example 2, one can use Dosie™ to calculate the PDT-dose for the target. The PS is Photofrin™. The simulation parameters for Photofrin are: β=11.9, δ=33, ξ=3.7E-03, σ=7.6E-05. The oxygen flow rate g=0.8 μM/s, $S_A$=0.319, the oxygen concentration=83 μM and [PS]=4 μM. The treatment time is 2400 s (40 minutes). The results are shown in FIG. 14 and FIG. 15. FIG. 14 shows the outside surface 1400 of the target. FIG. 15 is a cross sectional view showing the inside surface of the hole 1410. The graphical outputs are set to show the regions of the target area that receive a threshold PDT-dose of 439 μM $J/cm^2$ (the threshold PDT-dose shown in TABLE 2 for mice). In the 'lighter' regions 1420, the PDT-dose is equal to or greater than 439 μM $J/cm^2$. In the 'darker' regions 1430 of the target, the PDT-dose is less than 439 μM $J/cm^2$, indicating that at least another light source fiber may be required to ensure that all the spatial elements receive the threshold PDT-dose. Preferably the threshold PDT-dose should be delivered at a fluence rate greater than a threshold fluence rate. Comparing FIG. 14 with FIG. 12 and comparing FIG. 15 with FIG. 13 shows that the fluence rate is greater than the threshold fluence rate of 8.4 $mW/cm^2$ in the areas where the PDT-dose is greater than the threshold PDT-dose of 439 μM $J/cm^2$.

Example 4: Determine $[^1O_2]_{dose}$ for the Target Region

Figure 16:
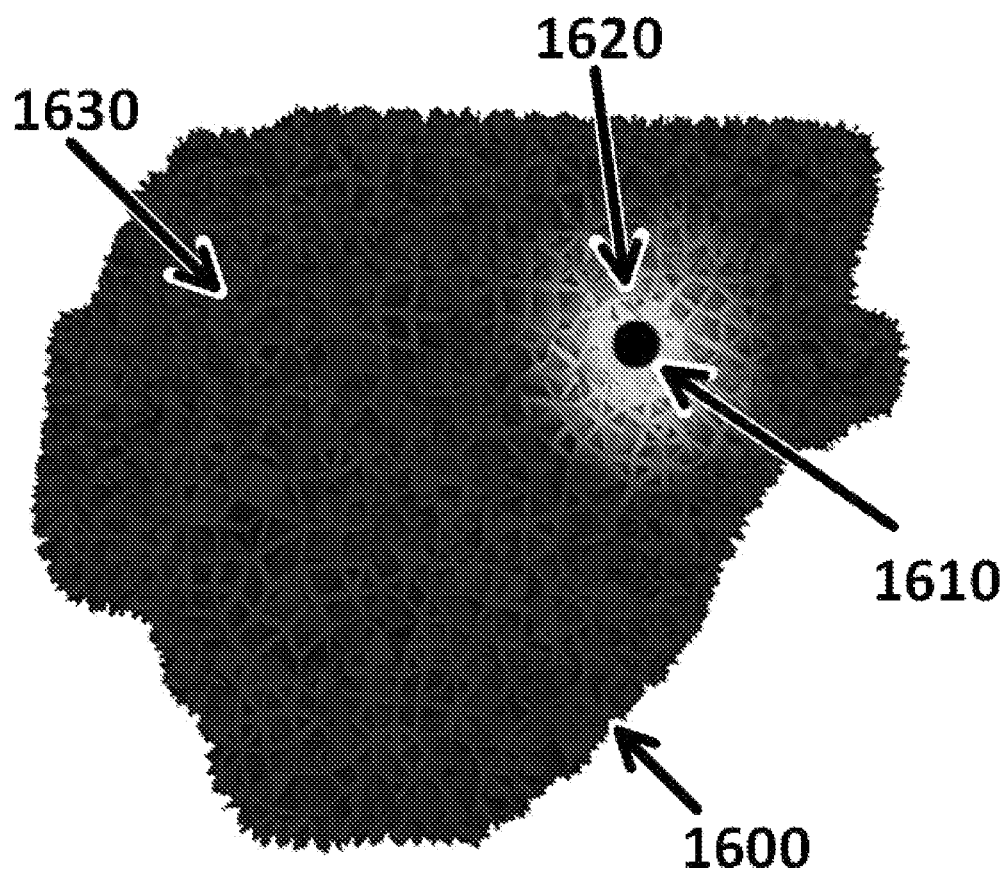
FIG. 16 shows a portion of a target region that receives a threshold singlet oxygen or ROS dose.
Figure 17:
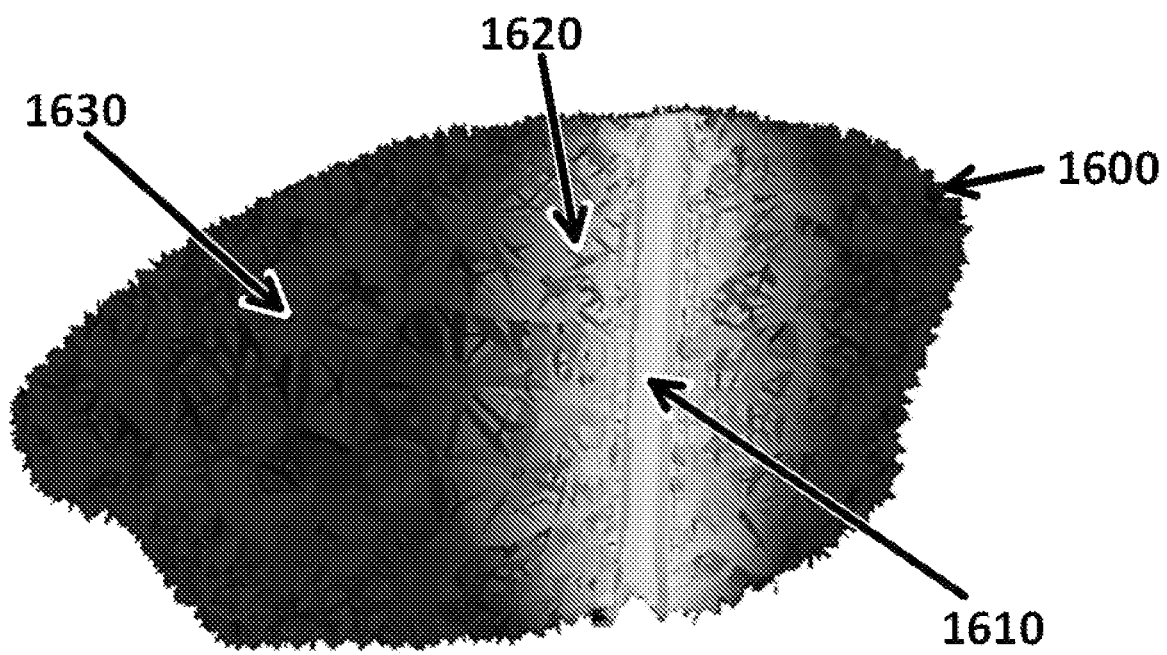
FIG. 17 shows a cross sectional view of a portion of a target region and a portion of the surface of the hole that receive a threshold singlet oxygen or ROS dose.

Using the calculated fluence rates for the tetrahedral mesh elements from Example 2, one can use Dosie™ to calculate the $[^1O_2]_{dose}$ for the target. The PS is Photofrin™. The simulation parameters for Photofrin are: β=11.9, δ=33, =3.7E-03, σ=7.6E-05. The oxygen flow rate g=0.8 μM/s, $S_A$=0.319, the oxygen concentration=83 μM and [PS]=4 μM. The treatment time is 2400 s (40 minutes). The results are shown in FIG. 16 and FIG. 17. FIG. 16 shows the outside surface 1600 of the target. FIG. 17 is a cross sectional view showing the inside surface of the hole 1610. The graphical outputs are set to show the regions of the target area that receive a threshold $[^1O_2]_{dose}$ of 1 mM (approximately the threshold $[^1O_2]_{dose}$ shown in TABLE 3 for mice). In the 'lighter' regions 1620, the $[^1O_2]_{dose}$ is equal to or greater than 1 mM. In the 'darker' regions 1630 of the target, the $[^1O_2]_{dose}$ is less than 1 mM. Preferably the threshold $[^1O_2]_{dose}$ should be delivered at a fluence rate greater than a threshold fluence rate. Comparing FIG. 16 with FIG. 12 and comparing FIG. 17 with FIG. 13 shows that the fluence rate is greater than the threshold fluence rate of 8.4 $mW/cm^2$ in the areas where the $[^1O_2]_{dose}$ is greater than the threshold $[^1O_2]_{dose}$ of 1 mM.

Examples 2, 3 and 4 show that one interstitial fiber may not sufficient to generate a threshold fluence rate, a threshold PDT-dose or a threshold $[^1O_2]_{dose}$, respectively, over the entire target volume or boundary. Additional interstitial fibers may be needed for effective treatments.

While several exemplary aspects and embodiments have been discussed above, those having skill in the art will recognize certain modifications, permutations, additions and sub-combinations that are also within the spirit and scope of this invention.

FURTHER CONSIDERATIONS

In some embodiments, any of the clauses herein may depend from any one of the independent clauses or any one of the dependent clauses. In one aspect, any of the clauses (e.g., dependent or independent clauses) may be combined with any other one or more clauses (e.g., dependent or independent clauses). In one aspect, a claim may include some or all of the words (e.g., steps, operations, means or components) recited in a clause, a sentence, a phrase or a paragraph. In one aspect, a claim may include some or all of the words recited in one or more clauses, sentences, phrases or paragraphs. In one aspect, some of the words in each of the clauses, sentences, phrases or paragraphs may be removed. In one aspect, additional words or elements may be added to a clause, a sentence, a phrase or a paragraph. In one aspect, the subject technology may be implemented without utilizing some of the components, elements, functions or operations described herein. In one aspect, the subject technology may be implemented utilizing additional components, elements, functions or operations.

The subject technology is illustrated, for example, according to various aspects described below. Various examples of aspects of the subject technology are described as numbered clauses (1, 2, 3, etc.) for convenience. These are provided as examples and do not limit the subject technology. It is noted that any of the dependent clauses may be combined in any combination, and placed into a respective independent clause, e.g., clause 1 or clause 5. The other clauses can be presented in a similar manner.

Clause 1: A method of administering interstitial photodynamic therapy by delivering treatment dose to a target region of a patient, the method comprising: receiving, at a processor, information associated with the target region, an initial photo-sensitizer concentration, a plurality of initial photosensitizer photokinetic rate parameters, and a threshold treatment dose for a photosensitizer, the threshold treatment dose being a threshold photodynamic therapy-dose or a threshold reactive oxygen species dose; determining a location in the target region for inserting at least one interstitial treatment fiber to deliver the treatment light; determining, by the processor, initial values for therapeutic light power, and light emitting length and therapeutic treatment time for the at least one interstitial treatment fiber; determining, by the processor, computational spatial elements for the target region and for the location of emitting surfaces of the at least one interstitial treatment fiber, and a fluence rate for delivering treatment light to each of the computational spatial elements; determining, by the processor, a treatment dose based on the fluence rate, the plurality of photosensitizer photokinetic rate parameters, and a photokinetic rate equation; and generating, by the processor, a command for controlling a treatment light source to deliver the treatment dose to the target region via the at least one interstitial treatment fiber.

Clause 2: The method of clause 1, wherein information associated with the target region comprises shape information of the target region, an initial tissue oxygen concentration for the target region, an initial oxygen flow rate for the target region, and initial optical properties for the target region.

Clause 3: The method of any of the preceding clauses, further comprising: determining, by the processor, a value of one or both of a portion of interior volume and a portion of a boundary region of the target region to which the delivered treatment dose is greater than the threshold treatment dose.

Clause 4: The method of clause 3 further comprising: in response to a determination that the value of one or both of the portion of interior volume and the portion of the boundary region of the target region to which the delivered treatment dose is greater than the threshold treatment dose is less than 80%, causing, by the processor, the treatment light source to increase one or both of therapeutic light power and therapeutic treatment time.

Clause 5: The method of any of the preceding clauses, further comprising: determining, by the processor, a value of one or both of a portion of interior volume and a portion of a boundary region of the target region to which the delivered treatment dose is greater than the threshold treatment dose and the applied fluence rate is greater than the threshold fluence rate.

Clause 6: The method of clause 5, further comprising: in response to a determination that the value of one or both of the portion of interior volume and the portion of the boundary region of the target region to which the delivered treatment dose is greater than the threshold treatment dose and the applied fluence rate is greater than the threshold fluence rate, is less than 80%, generating, by the processor, a command for controlling the treatment light source to increase one or both of therapeutic light power and therapeutic treatment time.

Clause 7: The method of any of the preceding clauses, further comprising: determining whether values for one or more of the initial photosensitizer concentration, any of the plurality of initial photosensitizer photokinetic rate parameters, an initial tissue oxygen concentration, initial tissue optical properties and an initial oxygen flow rate for the target region have changed.

Clause 8: The method of clause 7, further comprising: in response to a determination that one or more of the values of the initial photosensitizer concentration, any of the plurality of initial photosensitizer photokinetic rate parameters, an initial tissue oxygen concentration, initial tissue optical properties and an initial oxygen flow rate for the target region have changed, determining, by the processor, an updated treatment dose based on changed values of the one or more of the initial photosensitizer concentration, any of the plurality of initial photosensitizer photokinetic rate parameters, an initial tissue oxygen concentration, initial tissue optical properties and an initial oxygen flow rate.

Clause 9: The method of any of the preceding clauses, wherein the computational spatial elements comprise tetrahedral mesh elements or voxel elements.

Clause 10: A system for delivering a treatment dose to a target region of a patient for interstitial photodynamic therapy, the system comprising: a treatment light source coupled to at least one interstitial treatment fiber; a diagnostic light source coupled to at least one interstitial diagnostic fiber; at least one interstitial detector to detect diagnostic light generated by the diagnostic light source and/or treatment light generated by the treatment light source and/or photosensitizer fluorescence generated by the diagnostic light source or the treatment light source; and a processor configured to: receive information associated with the target region, an initial photosensitizer concentration, a plurality of initial photosensitizer photokinetic rate parameters, and a threshold treatment dose for a photosensitizer, the threshold treatment dose being a threshold photodynamic therapy-dose or a threshold reactive oxygen species dose; determine a location in the target region for inserting the at least one interstitial treatment fiber to deliver the treatment light; determine initial values for therapeutic light power, and light emitting length and therapeutic treatment time for the at least one interstitial treatment fiber; determine computational spatial elements for the target region and for the location of emitting surfaces of the at least one interstitial treatment fiber, and a fluence rate for delivering treatment light to each of the computational spatial elements; determine a treatment dose based on the fluence rate, the plurality of photosensitizer photokinetic rate parameters, and a photokinetic rate equation; and generate a command for controlling the treatment light source to deliver via the at least one interstitial treatment fiber the treatment dose to the target region.

Clause 11: The system of clause 10, further comprising at least one spectrometer coupled to the at least one interstitial detector to detect one or more of treatment light intensity, diagnostic light intensity and fluorescence light intensity generated by the treatment light source or the diagnostic light source.

Clause 12: The system of any of clauses 10-11, further comprising a plurality of light-transmitting catheters enclosing the at least one interstitial treatment fiber, the at least one interstitial diagnostic fiber and the at least one interstitial detector.

Clause 13: The system of any of clauses 10-12, wherein the treatment light source and/or the diagnostic light source comprise a laser or a light emitting diode.

Clause 14: The system of any of clauses 10-13, wherein the processor is further configured to determine a value of one or both of a portion of interior volume and a portion of a boundary region of the target region to which the delivered treatment dose is greater than the threshold treatment dose.

Clause 15: The system of clause 14, wherein the processor is further configured to cause, in response to a determination that the value of one or both of the portion of interior volume and the portion of the boundary region of the target region to which the delivered treatment dose is greater than the threshold treatment dose is less than 80%, the treatment light source to increase one or both of therapeutic light power and therapeutic treatment time.

Clause 16: The system of any of clauses 10-15, wherein the processor is further configured to determine a value of one or both of a portion of interior volume and a portion of a boundary region of the target region to which the delivered treatment dose is greater than the threshold treatment dose and the applied fluence rate is greater than the threshold fluence rate.

Clause 17: The system of clause 16, wherein the processor is further configured to generate, in response to a determination that the value of one or both of the portion of interior volume and the portion of the boundary region of the target region to which the delivered treatment dose is greater than the threshold treatment dose and the applied fluence rate is greater than the threshold fluence rate is less than 80%, a command for controlling the treatment light source to increase one or both of therapeutic light power and therapeutic treatment time.

Clause 18: The system of any of clauses 10-17, wherein the processor is further configured to: determine whether values for one or more of the initial photosensitizer concentration, any of the plurality of initial photosensitizer photokinetic rate parameters, an initial tissue oxygen concentration, initial tissue optical properties and an initial oxygen flow rate for the target region have changed, and in response to a determination that one or more of the values have changed, determine an updated treatment dose based on changed values of the one or more of the initial photosensitizer concentration, any of the plurality of initial photosensitizer photokinetic rate parameters, an initial tissue oxygen concentration, initial tissue optical properties and an initial oxygen flow rate.

Clause 19: The system of any of clause 10-18, wherein the computational spatial elements comprise tetrahedral mesh elements or voxel elements.

Clause 20: The system of any of clauses 10-19, further comprising a display configured to enable a user to visualize a two-dimensional or three-dimensional image of the treatment dose and/or two-dimensional or a three-dimensional image of under- and over-doses overlaid onto a two-dimensional and/or a three-dimensional image of shape information for the target region.

Clause 21: A method for planning an interstitial photodynamic therapy treatment dose to be delivered to a target region of a patient for, the method comprising: receiving, at a processor, information associated with the target region, an initial photo-sensitizer concentration, a plurality of initial photosensitizer photokinetic rate parameters, and a threshold treatment dose for a photosensitizer, the threshold treatment dose being a threshold photodynamic therapy-dose or a threshold reactive oxygen species dose; determining a location in the target region for inserting at least one interstitial treatment fiber to deliver the treatment light; determining, by the processor, initial values for therapeutic light power, and light emitting length and therapeutic treatment time for the at least one interstitial treatment fiber; determining, by the processor, computational spatial elements for the target region and for the location of emitting surfaces of the at least one interstitial treatment fiber, and a fluence rate for delivering treatment light to each of the computational spatial elements; and determining, by the processor, a treatment dose based on the fluence rate, the plurality of photosensitizer photokinetic rate parameters, and a photokinetic rate equation.

Clause 22: The method of clause 21, further comprising: determining, by the processor, a value of one or both of a portion of interior volume and a portion of a boundary region of the target region to which the delivered treatment dose is greater than the threshold treatment dose; and determining, in response to a determination that the value is less than 80%, an increase in one or more of therapeutic light power, light emitting length and therapeutic treatment time such that the treatment dose delivered to at least 80% of one or both of interior volume and boundary region of the target region is greater than the threshold treatment dose.

Clause 23: The method of any of clauses 21-22, further comprising: determining whether values for one or more of the initial photosensitizer concentration, any of the plurality of initial photosensitizer photokinetic rate parameters, an initial tissue oxygen concentration, initial tissue optical properties and an initial oxygen flow rate for the target region have changed; and determining, in response to a determination that one or more of the values have changed, an updated treatment dose based on changed values of the one or more of the initial photosensitizer concentration, any of the plurality of initial photosensitizer photokinetic rate parameters, an initial tissue oxygen concentration, initial tissue optical properties and an initial oxygen flow rate.

Clause 24: The method of any of clauses 21-23, further comprising: determining whether a location of the at least one interstitial treatment fiber relative to the target region has changed; and determining, in response to a determination that the location has changed, an updated treatment dose based on the changed location.

Clause 25: The method of any of clauses 21-24, further comprising: determining, by the processor, a value of one or both of a portion of interior volume and a portion of a boundary region of the target region to which the delivered treatment dose is greater than the threshold treatment dose and the applied fluence rate is greater than the threshold fluence rate; and determining, in response to a determination that the value is less than 80%, an increase in one or more of therapeutic light power, light emitting length and therapeutic treatment time such that the treatment dose delivered to at least 80% of one or both of interior volume and boundary region of the target region is greater than the threshold treatment dose and the applied fluence rate is greater than the threshold fluence rate.

Clause 26: A system for planning an interstitial photodynamic therapy, the system comprising: a non-transitory computer-readable memory to store instructions; and a processor to execute the instructions stored on the memory, the instructions causing the processor to: receive information associated with the target region, an initial photosensitizer concentration, a plurality of initial photosensitizer photokinetic rate parameters, and a threshold treatment dose for a photosensitizer, the threshold treatment dose being a threshold photodynamic therapy-dose or a threshold reactive oxygen species dose; determine a location in the target region for inserting at least one interstitial treatment fiber to deliver the treatment light; determine initial values for therapeutic light power, and light emitting length and therapeutic treatment time for the at least one interstitial treatment fiber; determine computational spatial elements for the target region and for the location of emitting surfaces of the at least one interstitial treatment fiber, and a fluence rate for delivering treatment light to each of the computational spatial elements; and determine a treatment dose based on the fluence rate, the plurality of photosensitizer photokinetic rate parameters, and a photokinetic rate equation.

Clause 27: The system of clause 26, further comprising at least one spectrometer coupled to the at least one interstitial detector to detect one or more of treatment light intensity, diagnostic light intensity and fluorescence light intensity generated by a treatment light source or a diagnostic light source.

Clause 28: The system of any of clauses 26-27, further comprising a plurality of light-transmitting catheters enclosing the at least one interstitial treatment fiber, at least one interstitial diagnostic fiber and/or at least one interstitial detector.

Clause 29: The system of any of clauses 26-28, further comprising a treatment light source and/or a diagnostic light source, each of which comprise a laser or a light emitting diode.

Clause 30: The system of clause 26, wherein the processor is further configured to determine a value of one or both of a portion of interior volume and a portion of a boundary region of the target region to which the delivered treatment dose is greater than the threshold treatment dose.

Clause 31: The system of clause 30, wherein the processor is further configured to determine, in response to a determination that the value of one or both of the portion of interior volume and the portion of the boundary region of the target region to which the delivered treatment dose is greater than the threshold treatment dose is less than 80%, an increase in one or more of therapeutic light power, light emitting length and therapeutic treatment time such that at least 80% of the interior volume and/or the boundary region of the target region receives a treatment dose greater than the threshold treatment dose.

Clause 32: The system of any of clauses 26-31, wherein the processor is further configured to determine a value of one or both of a portion of interior volume and a portion of a boundary region of the target region to which the delivered treatment dose is greater than the threshold treatment dose and the applied fluence rate is greater than the threshold fluence rate.

Clause 33: The system of clause 32, wherein the processor is further configured to determine, in response to a determination that the value of one or both of the portion of interior volume and the portion of the boundary region of the target region to which the delivered treatment dose is greater than the threshold treatment dose and the applied fluence rate is greater than the threshold fluence rate is less than 80%, an increase in one or more of therapeutic light power, light emitting length and therapeutic treatment time such that at least 80% of the interior volume and/or the boundary region of the target region receives a treatment dose greater than the threshold treatment dose and a fluence rate is greater than the threshold fluence rate.

Clause 34: The system of any of clauses 26-33, wherein the processor is further configured to: determine whether values for one or more of the initial photosensitizer concentration, any of the plurality of initial photosensitizer photokinetic rate parameters, an initial tissue oxygen concentration, initial tissue optical properties and an initial oxygen flow rate for the target region have changed, and in response to a determination that one or more of the values have changed, determine an updated treatment dose based on changed values of the one or more of the initial photosensitizer concentration, any of the plurality of initial photosensitizer photokinetic rate parameters, an initial tissue oxygen concentration, initial tissue optical properties and an initial oxygen flow rate.

Clause 35: The system of any of clauses 26-34, wherein the computational spatial elements comprise tetrahedral mesh elements or voxel elements.

Clause 36: The system of any of clauses 26-35, further comprising a display configured to enable a user to visualize a two-dimensional or three-dimensional image of the treatment dose and/or a two-dimensional or three-dimensional image of under- and over-doses overlaid onto a two-dimensional and/or three-dimensional image of shape information for the target region.

Clause 37: A non-transitory machine-readable medium storing instructions to cause one or more processors to perform operations comprising: receiving, at a processor, information associated with the target region, an initial photo-sensitizer concentration, a plurality of initial photosensitizer photokinetic rate parameters, and a threshold treatment dose for a photosensitizer, the threshold treatment dose being a threshold photodynamic therapy-dose or a threshold reactive oxygen species dose; determining a location in the target region for inserting at least one interstitial treatment fiber to deliver the treatment light; determining, by the processor, initial values for therapeutic light power, and light emitting length and therapeutic treatment time for the at least one interstitial treatment fiber; determining, by the processor, computational spatial elements for the target region and for the location of emitting surfaces of the at least one interstitial treatment fiber, and a fluence rate for delivering treatment light to each of the computational spatial elements; and determining, by the processor, a treatment dose based on the fluence rate, the plurality of photosensitizer photokinetic rate parameters, and a photokinetic rate equation.

Clause 38: The non-transitory machine-readable medium of clause 37, wherein information associated with the target region comprises shape information of the target region, an initial tissue oxy-gen concentration for the target region, an initial oxygen flow rate for the target region, and initial optical properties for the target region.

The foregoing description is provided to enable a person skilled in the art to practice the various configurations described herein. While the subject technology has been particularly described with reference to the various figures and configurations, it should be understood that these are for illustration purposes only and should not be taken as limiting the scope of the subject technology.

There may be many other ways to implement the subject technology. Various functions and elements described herein may be partitioned differently from those shown without departing from the scope of the subject technology. Various modifications to these configurations will be readily apparent to those skilled in the art, and generic principles defined herein may be applied to other configurations. Thus, many changes and modifications may be made to the subject technology, by one having ordinary skill in the art, without departing from the scope of the subject technology.

It is understood that the specific order or hierarchy of steps in the processes disclosed is an illustration of exemplary approaches. Based upon design preferences, it is understood that the specific order or hierarchy of steps in the processes may be rearranged. Some of the steps may be performed simultaneously. The accompanying method claims present elements of the various steps in a sample order, and are not meant to be limited to the specific order or hierarchy presented.

As used herein, the term "about" preceding a quantity indicates a variance from the quantity. The variance may be caused by manufacturing tolerances or may be based on differences in measurement techniques. The variance may be up to 10% from the listed value in some instances. Those of ordinary skill in the art would appreciate that the variance in a particular quantity may be context dependent and thus, for example, the variance in a dimension at a micro or a nano scale may be different than variance at a meter scale.

As used herein, the phrase "at least one of" preceding a series of items, with the term "and" or "or" to separate any of the items, modifies the list as a whole, rather than each member of the list (i.e., each item). The phrase "at least one of" does not require selection of at least one of each item listed; rather, the phrase allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

Terms such as "top," "bottom," "front," "rear" and the like as used in this disclosure should be understood as referring to an arbitrary frame of reference, rather than to the ordinary gravitational frame of reference. Thus, a top surface, a bottom surface, a front surface, and a rear surface may extend upwardly, downwardly, diagonally, or horizontally in a gravitational frame of reference.

Furthermore, to the extent that the term "include," "have," or the like is used in the description or the claims, such term is intended to be inclusive in a manner similar to the term "comprise" as "comprise" is interpreted when employed as a transitional word in a claim.

The word "exemplary" is used herein to mean "serving as an example, instance, or illustration." Any embodiment described herein as "exemplary" is not necessarily to be construed as preferred or advantageous over other embodiments.

A reference to an element in the singular is not intended to mean "one and only one" unless specifically stated, but rather "one or more." Pronouns in the masculine (e.g., his) include the feminine and neuter gender (e.g., her and its) and vice versa. The term "some" refers to one or more. Underlined and/or italicized headings and subheadings are used for convenience only, do not limit the subject technology, and are not referred to in connection with the interpretation of the description of the subject technology. All structural and functional equivalents to the elements of the various configurations described throughout this disclosure that are known or later come to be known to those of ordinary skill in the art are expressly incorporated herein by reference and intended to be encompassed by the subject technology. Moreover, nothing disclosed herein is intended to be dedicated to the public regardless of whether such disclosure is explicitly recited in the above description.

What is claimed is:

1. A method of administering interstitial photodynamic therapy by delivering treatment dose to a target region of a patient, the method comprising:
   receiving, at a processor, information associated with the target region, an initial photosensitizer concentration, a plurality of initial photosensitizer photokinetic rate parameters, and a threshold treatment dose for a photosensitizer, the threshold treatment dose being a threshold photodynamic therapy-dose or a threshold reactive oxygen species dose;
   determining a location in the target region for inserting at least one interstitial treatment fiber to deliver the treatment light;
   determining, by the processor, initial values for therapeutic light power, and light emitting length and therapeutic treatment time for the at least one interstitial treatment fiber; determining, by the processor, computational spatial elements for the target region and for the location of emitting surfaces of the at least one interstitial treatment fiber, and a fluence rate for delivering treatment light to each of the computational spatial elements;
   determining, by the processor, a treatment dose based on the fluence rate, the plurality of photosensitizer photokinetic rate parameters, and a photokinetic rate equation;
   determining, by the processor, a value of one or both of a portion of interior volume and a portion of a boundary region of the target region to which the delivered treatment dose is greater than the threshold treatment dose; and
   generating, by the processor, a command for controlling a treatment light source to deliver the treatment dose to the target region via the at least one interstitial treatment fiber.

2. The method of claim 1, wherein information associated with the target region comprises shape information of the target region, an initial tissue oxygen concentration for the target region, an initial oxygen flow rate for the target region, and initial optical properties for the target region.

3. The method of claim 1, further comprising:
   in response to a determination that the value of one or both of the portion of interior volume and the portion of the boundary region of the target region to which the delivered treatment dose is greater than the threshold treatment dose is less than 80%, causing, by the processor, the treatment light source to increase one or both of therapeutic light power and therapeutic treatment time.

4. The method of claim 1, further comprising:
   determining, by the processor, a value of one or both of a portion of interior volume and a portion of a boundary region of the target region to which the delivered treatment dose is greater than the threshold treatment dose and the applied fluence rate is greater than the threshold fluence rate.

5. The method of claim 4, further comprising:
   in response to a determination that the value of one or both of the portion of interior volume and the portion of the boundary region of the target region to which the delivered treatment dose is greater than the threshold treatment dose and the applied fluence rate is greater than the threshold fluence rate, is less than 80%, generating, by the processor, a command for controlling the treatment light source to increase one or both of therapeutic light power and therapeutic treatment time.

6. The method of claim 1, further comprising:
determining whether values for one or more of the initial photosensitizer concentration, any of the plurality of initial photosensitizer photokinetic rate parameters, an initial tissue oxygen concentration, initial tissue optical properties and an initial oxygen flow rate for the target region have changed.

7. The method of claim 6, further comprising:
in response to a determination that one or more of the values of the initial photosensitizer concentration, any of the plurality of initial photosensitizer photokinetic rate parameters, an initial tissue oxygen concentration, initial tissue optical properties and an initial oxygen flow rate for the target region have changed, determining, by the processor, an updated treatment dose based on changed values of the one or more of the initial photosensitizer concentration, any of the plurality of initial photosensitizer photokinetic rate parameters, an initial tissue oxygen concentration, initial tissue optical properties and an initial oxygen flow rate.

8. The method of claim 1, wherein the computational spatial elements comprise tetrahedral mesh elements or voxel elements.

9. A method for planning an interstitial photodynamic therapy treatment dose to be delivered to a target region of a patient for, the method comprising:
receiving, at a processor, information associated with the target region, an initial photosensitizer concentration, a plurality of initial photosensitizer photokinetic rate parameters, and a threshold treatment dose for a photosensitizer, the threshold treatment dose being a threshold photodynamic therapy-dose or a threshold reactive oxygen species dose;
determining a location in the target region for inserting at least one interstitial treatment fiber to deliver the treatment light;
determining, by the processor, initial values for therapeutic light power, and light emitting length and therapeutic treatment time for the at least one interstitial treatment fiber;
determining, by the processor, computational spatial elements for the target region and for the location of emitting surfaces of the at least one interstitial treatment fiber, and a fluence rate for delivering treatment light to each of the computational spatial elements;
determining, by the processor, a treatment dose based on the fluence rate, the plurality of photosensitizer photokinetic rate parameters, and a photokinetic rate equation;
determining, by the processor, a value of one or both of a portion of interior volume and a portion of a boundary region of the target region to which the delivered treatment dose is greater than the threshold treatment dose; and
determining, in response to a determination that the value is less than 80%, an increase in one or more of therapeutic light power, light emitting length and therapeutic treatment time such that the treatment dose delivered to at least 80% of one or both of interior volume and boundary region of the target region is greater than the threshold treatment dose.

10. The method of claim 9, further comprising:
determining whether values for one or more of the initial photosensitizer concentration, any of the plurality of initial photosensitizer photokinetic rate parameters, an initial tissue oxygen concentration, initial tissue optical properties and an initial oxygen flow rate for the target region have changed; and
determining, in response to a determination that one or more of the values have changed, an updated treatment dose based on changed values of the one or more of the initial photosensitizer concentration, any of the plurality of initial photosensitizer photokinetic rate parameters, an initial tissue oxygen concentration, initial tissue optical properties and an initial oxygen flow rate.

11. The method of claim 9, further comprising:
determining whether a location of the at least one interstitial treatment fiber relative to the target region has changed; and
determining, in response to a determination that the location has changed, an updated treatment dose based on the changed location.

12. The method of claim 9, further comprising:
determining, by the processor, a value of one or both of a portion of interior volume and a portion of a boundary region of the target region to which the delivered treatment dose is greater than the threshold treatment dose and the applied fluence rate is greater than the threshold fluence rate; and
determining, in response to a determination that the value is less than 80%, an increase in one or more of therapeutic light power, light emitting length and therapeutic treatment time such that the treatment dose delivered to at least 80% of one or both of interior volume and boundary region of the target region is greater than the threshold treatment dose and the applied fluence rate is greater than the threshold fluence rate.

* * * * *